United States Patent
Kemp et al.

(10) Patent No.: US 11,807,909 B1
(45) Date of Patent: Nov. 7, 2023

(54) METHODS FOR SPECIES-LEVEL RESOLUTION OF MICROORGANISMS

(71) Applicant: ZYMO RESEARCH CORPORATION, Irvine, CA (US)

(72) Inventors: Ryan Kemp, Irvine, CA (US); Mike Weinstein, Irvine, CA (US); Shuiquan Tang, Irvine, CA (US)

(73) Assignee: ZYMO RESEARCH CORPORATION, Irvine, CA (US)

( * ) Notice: Subject to any disclaimer, the term of this patent is extended or adjusted under 35 U.S.C. 154(b) by 388 days.

(21) Appl. No.: 16/933,920

(22) Filed: Jul. 20, 2020

Related U.S. Application Data

(60) Provisional application No. 62/899,531, filed on Sep. 12, 2019.

(51) Int. Cl.
    *C12P 19/34* (2006.01)
    *C12Q 1/689* (2018.01)
    *C12Q 1/6869* (2018.01)

(52) U.S. Cl.
    CPC .................. *C12Q 1/689* (2013.01); *C12Q 1/6869* (2013.01)

(58) Field of Classification Search
    CPC .................................................. C12Q 1/6869
    See application file for complete search history.

(56) References Cited

U.S. PATENT DOCUMENTS

| | | |
|---|---|---|
| 5,075,430 A | 12/1991 | Little |
| 5,650,506 A | 7/1997 | Woodard et al. |
| 5,705,628 A | 1/1998 | Hawkins |
| 5,898,071 A | 4/1999 | Hawkins |
| 6,027,945 A | 2/2000 | Smith et al. |
| 6,284,470 B1 | 9/2001 | Bitner et al. |
| 6,673,631 B1 | 1/2004 | Tereba et al. |
| 7,078,224 B1 | 7/2006 | Bitner et al. |
| 9,051,563 B2 | 6/2015 | Forman et al. |
| 9,546,400 B2 | 1/2017 | Turner et al. |
| 10,081,835 B2 | 9/2018 | Akeson et al. |
| 2010/0137143 A1 | 6/2010 | Rothberg et al. |
| 2010/0304982 A1 | 12/2010 | Hinz et al. |
| 2018/0195111 A1* | 7/2018 | Gosiewski et al. .. C12Q 1/6869 |
| 2021/0228655 A1* | 7/2021 | O'Toole et al. .......... A61P 1/00 |

OTHER PUBLICATIONS

Rychlik et al., Nucleic Acids Research 17(21), 8543-8551 (1989). (Year: 1989).*

* cited by examiner

*Primary Examiner* — Kenneth R Horlick
(74) *Attorney, Agent, or Firm* — Parker Highlander PLLC

(57) ABSTRACT

Methods and devices are provided for the identification and/or quantification of microbes. In particular, the methods comprise: (a) extracting DNA from a microbial sample; (b) performing 16S ribosomal RNA gene-targeted sequencing to obtain DNA sequences; and (c) analyzing the DNA sequences to identify the species of the one or more microbes.

24 Claims, 2 Drawing Sheets
(2 of 2 Drawing Sheet(s) Filed in Color)

Specification includes a Sequence Listing.

METHODS FOR SPECIES-LEVEL RESOLUTION OF MICROORGANISMS

This application claims the benefit of U.S. Provisional Pat. Application No. 62/899,531, filed Sep. 12, 2019, which is incorporated herein by reference in their entirety.

This application contains a Sequence Listing, which has been submitted electronically and is hereby incorporated by reference in its entirety. Said Sequence Listing, created on Mar. 23, 2023, is named ZYMOP0042US_ST25.txt and is 3,953 bytes in size.

BACKGROUND

1. Field of the Invention

The present invention relates generally to the field of molecular biology. More particularly, it concerns identification and/or quantification of a microorganism.

2. Description of Related Art

In many microbiology-related applications (e.g., infectious disease diagnosis and food safety testing), the need to determine the identity and quantity of the microbes is a common requirement. In practice, most applications use culture-based microbial analysis, PCR or arrays. The culture approach relies on isolating the microbes on agar plates followed by taxonomy identification of the isolated microbes from colonies of agar plates often by subsequent PCR, sequencing or arrays (e.g., the Biofire platform). The isolated microbes can be quantified through colony counting. However, problems with culture-based microbial detection have been widely recognized including limited coverage as many microbes are not culturable, slow as many culturable microbes take days or even weeks to grow colonies, difficult as many anaerobes are very difficult to cultivate, and multiple tests as it takes several tests to cover potential pathogens, e.g. aerobes, anaerobes and fungi.

Another approach that is routinely used is quantitative PCR (qPCR). With primers and/or probes that target specific microbes, qPCR can produce results within a couple of hours. qPCR has the advantage of being relatively fast and low cost but can only cover limited targets, even with multiplex PCR and multiple-well of amplification. A cost-effective qPCR panel normally covers less than 30 targets. Thus, there is an unmet need for a novel approach that enables an almost species-level resolution of a wide array of microorganisms, including those relevant to human health and disease.

SUMMARY

In a first embodiment, the present disclosure provides a method for the identification and/or quantification of one or more microbes comprising: (a) extracting DNA from a microbial sample; (b) performing 16S ribosomal RNA gene-targeted sequencing to obtain DNA sequences; and (c) analyzing the DNA sequences to identify the species of the one or more microbes. In certain aspects, the microbial sample is a human sample. In other aspects, the microbial sample is an environmental sample. In some specific aspects, the environmental sample may comprise water, biofilms, soil, air, or host-derived samples. In further aspects, the host-derived sample comprises body fluids, saliva, urine, fecal, surface swab, root, leaf or bark samples. In another aspect, the host-derived sample is a fecal sample.

In some aspects, analyzing DNA sequences is further defined as performing bioinformatics analysis to identify the species of the one or more microbes. In a specific aspect, the bioinformatics analysis comprises using modeling of error accumulation across the lengths of both the forward and reverse reads for read trimming and filtering optimization (FIGARO) followed by a denoising algorithm to correct for sequencer-generated artifact (DADA2) to infer amplicon sequences. In additional aspects, the bioinformatics analysis further comprises assigning taxonomy to amplicon sequences. In a particular aspect, assigning taxonomy does not comprise clustering amplicon sequences into operation units (OTUs). In other aspects, assigning taxonomy comprises using sequence matches with higher or perfect identity to known reference sequences.

In further aspects, the method is performed in less than 3 days. In another aspect, the method is performed in 2 days. In certain aspects, the method does not comprise microbial culture or array analysis. In some aspects, the one or more microbes are of the phylum *Euryarchaeota, Actinobacteria, Bacteroidetes, Firmicutes, Fusobacteria, Lentisphaerae, Proteobacteria, Synergistetes,* and/or *Verrucomicrobia*. In other aspects, the one or more microbes are of the genus *Blautia, Butyrivibrio, Coprococcus, Dorea, Eubacterium, Fusicatenibacter, Lachnoclostridium, Lachnospira, Pseudobutyrivibrio,* and/or *Roseburia*. In certain specific aspects, the one or more microbes are of the species *Methanobrevibacter smithii, Bifidobacterium adolescentis, Bifidobacterium angulatum, Bifidobacterium ruminantium, Collinsella aerofaciens, Bacteroides fragilis, Prevotella copri, Sphingobacteriaceae sp., Catenibacterium mitsuokai, Clostridium difficile, Dialister invisus, Eubacterium rectale, Lactobacillus fermentum, Fusobacterium nucleatum, Victivallis vadensis, Bilophila wadsworthia, Escherichia coli, Sutterella wadsworthensis, Pyramidobacter piscolens,* and/or *Akkermansia muciniphila*.

In still further aspects, the sequencing comprises using V1-V2 or V3-V4 primers. In one aspect, the sequencing comprises using V3-V4 primers. In another aspect, the sequencing comprises using primers with a higher diversity of potential target sequences. For example, the primer can be selected from those in Table A.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein. The patent or application file contains at least one drawing executed in color. Copies of this patent or patent application publication with color drawing(s) will be provided by the Office upon request and payment of the necessary fee.

DESCRIPTION OF ILLUSTRATIVE EMBODIMENTS

Certain embodiments of the present disclosure provide method for the identification and/or quantification of microorganisms, especially those relevant to human health and disease. Specifically, the method comprises the use of a next generation sequencing (NGS)-based 16S ribosomal RNA gene-targeted sequencing approach. The method has high sensitivity and offers dramatically larger coverage compared to culture-based or qPCR methods. The turnaround time of the present method may be about 2 days.

Importantly, the present method provides species-level resolution of microorganisms as compared to previous methods which can be limited to genus-level resolution for bacterial profiling due to technical challenges. The present method comprises the isolation of nucleic acids from a microbial sample, generation of a library, and performing 16S ribosomal RNA gene-targeted sequencing to identify one or more microbes.

Nucleic acids, specifically genomic DNA, can be isolated from soil, microbial fermentation, water, biofilms, and/or eukaryotic cellular cultures or biological body fluids (e.g. sputum, feces, lymph fluid, cerebrospinal fluid (CSF), urine, serum, sweat, various aspirates, and other liquid biological sources) and solid tissues. In particular, the sample may comprise one or more different organisms, such as bacteria including gram negative and gram positive bacteria, archaea, fungi, spores, protozoans, single cell and multicellular parasites, oocyst and algae or other encapsulated or bound nucleic acids. The isolated nucleic acids may be used for microbiome or metagenome analyses.

The nucleic acids may be extracted by methods known in the art, preferably to avoid bias. For example, the Zymo-BIOMICS DNA Miniprep kit can be used to reduce bias during DNA extraction. Bias in extraction is associated with inefficient lysis of microorganisms. This leads to mis-quantification of organisms and specifically underrepresentation or erroneous non-detection of "tough-to-lyse" organisms such as *Listeria monocytogenes* or *Cryptococcus neoformans*. Thus, efficient lysis is needed to avoid bias in molecular (i.e., DNA/RNA) characterization of a sample.

Figure 2:
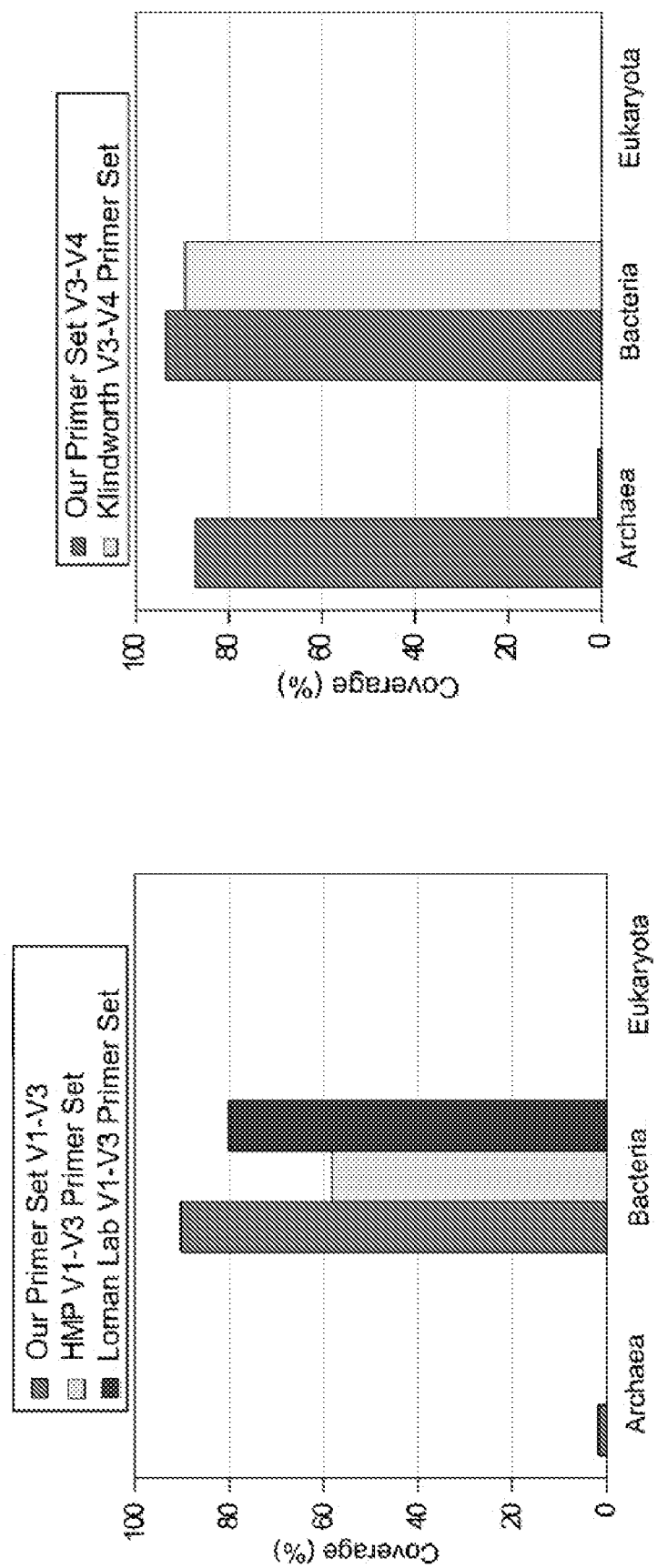
FIG. 2: Graphs show microbial coverage of our new 16S primers as compared to common primer sets from the same region.

The nucleic acids may then be used to produce a sequencing library for 16S sequencing. For example, the Quick-16S NGS Library Prep Kit may be used for library preparation along with one of the three primer sets (see Table A), theV1-V3 primers or V3-V4 primers. These two regions, i.e. V1-V3 and V3-V4, were chosen because they offer species-level resolution. The 16S library preparation process was performed in a 2-step PCR process, separating barcodes from the 16S amplification primers. This allows us to include more 16S primers in the 1$^{st}$ step PCR, therefore boosting the microbial coverage (FIG. 2). New 16S primers were introduced to provide coverage for microbes that are otherwise missed in common 16S primer sets. The sequences of the 16S primers were shown below in the Table A. After library preparation, the Illumina MiSeq with the 600 cycle kit was used for performing sequencing.

TABLE A

| Sequences of the primer pool targeting 16S V1-V3 and V3-V4 regions | | | |
|---|---|---|---|
| V13_forward | AGRGTTTGATYMTGGCTCAG (SEQ ID NO: 1) <br> AGGGTTCGATTCTGGCTCAG (SEQ ID NO: 2) <br> AGAATTTGATCTTGGTTCAG (SEQ ID NO: 3) <br> AGAGTTCGATCCTGGCTCAG (SEQ ID NO: 4) <br> AGAGTTTGATCCTGGCTTAG (SEQ ID NO: 5) <br> AGAGTTTGATCCTAGCTCAG (SEQ ID NO: 6) <br> ACTGCTATTGGGDTTCGAT (SEQ ID NO: 7) <br> ACTGCTATTGGGGTCCGAT (SEQ ID NO: 8) | V13_reverse | TBACCGCGGCTGCTGGCAC (SEQ ID NO: 9) <br> TTACCGCGGCGGCTGRCAC (SEQ ID NO: 10) <br> TTACCGCAGCTGCTGGCAC (SEQ ID NO: 11) |
| V34_forward | CCTACGGGDGGCWGCAG (SEQ ID NO: 12) <br> CCTAYGGGGCGCWGCAG (SEQ ID NO: 13) <br> CCTACGGGGTGCAGCAG (SEQ ID NO: 14) <br> CCTACGGGAGGCTGCAG (SEQ ID NO: 15) | V34_reverse | GACTACNVGGGTMTCTAATCC (SEQ ID NO: 16) <br> GACTACDCAGGTCTCTAATCT (SEQ ID NO: 17) <br> GAMTACCGGGGTTTCTAATCC (SEQ ID NO: 18) <br> GACTACCAGGGTATCTAAGCC (SEQ ID NO: 19) |

Bioinformatics analysis is then performed on the sequencing results to identify and/or quantify the one or more microbes. The bioinformatics pipeline that enables species-level resolution for bacteria identification can comprise three major components:

(a) Use of FIGARO prior to DADA2 to maximize sequence quality and retention post-filtering. Both FIGARO and DADA2 are open source programs, with FIGARO optimizing read trimming and filtering based upon mathematical modeling of error accumulation across the length of DNA sequence reads and DADA2 able to differentiate single-nucleotide differences between amplicons. In brief, FIGARO is a bioinformatics application that analyzes the entire set of sequencing reads or a subset of sequencing reads. If a subset of reads is used, often to decrease the amount of time required for analysis, this subset may be determined by either taking a set fraction of reads (e.g., every 20th read) or calculating the fraction of reads to take based upon the number of reads or amount of data in the sample. Reads are analyzed to determine percentiles for expected error accumulation at each point in the length of the read for the entire sample or subsample based upon their sequencing quality scores as reported by the sequencing device. This distribution of accumulated error values can either be based directly upon the observed data or, especially in the case of subsampled data, calculated using a mathematical model that is built including, but not limited to, exponential regression. The lengths of the forward and reverse reads are compared to the user-reported maximum expected amplicon length and desired overlap length between the reads and all possible combinations of read trimming locations that are capable of giving this set of amplicon lengths plus overlap with no excess read length are determined. After determining all possible trimming site combinations that are potentially desirable, as described above, each site combination is ranked based upon a scoring formula that is defined as starting with the percentage of reads expected to be retained, with a penalty that is calculated by the number of expected errors per read that must be allowed in the filtering process to get that percentage of reads to pass the filtering process greater than one and squared for both the forward and reverse reads. A list of potential trimming site combinations is returned for use in DADA2 or another similar downstream application along with figures showing the mathematical model developed for error accumulation on both the forward and reverse set of sequencing reads. This application may be run using a containerized computing platform such as Docker, run on the command line, run via graphical user interface (GUI), imported as a code package into a separate bioinformatics application, or loaded as a prepackaged application (such as Anaconda or Python pip).(b) Use of a unique taxonomy assignment function. Traditional 16S analysis clusters amplicon sequences into operation units (OTUs). In definition, each OTU is a group of sequences whose sequence identity between each is higher than a threshold, e.g. 97%. After OTU clustering, a representative sequence is picked to present the whole group or OTU. The taxonomy of the OTU is assigned by comparing the representative sequence to 16S gene reference database. Because OTU is a group of sequences within a certain sequence identity (e.g., 97%) and because the representative sequence is derived from raw sequencing reads directly without error corrections, using the taxonomy assigned from representative sequences which contains Illumina sequencing errors to represent the whole OTU is not preferred. Therefore, when the 16S analysis is performed in this way, it cannot predict species information effectively. By default, the Uclust function in the Qiime pipeline chooses to accept a maximum of 3 likely matches (hits) and the taxonomy is assigned based on more than 51 of the consensus of the matches. For the following three hits: hit1: *Listeria monocytogenes*, hit2: *Listeria ivanovii*, hit3: unknown genus, the taxonomy would be assigned as *Listeria sp.* even if the likelihood of a true match between the sequence in question and hit1 might be significantly higher than that between the sequence in question and hit2.

Thus, the present methods assign the taxonomy in a simpler and more straightforward way, with most likely matches. If the sequence identity between the query and hit1 is higher than that between the query and hit2, the query and hit3, the taxonomy of hit1 is assigned to the query. If there are matches of near-equal likelihood, the species information is concatenated together. In the example described above, if hit1 and hit2 have the sample sequence identity, the taxonomy is assigned as Listeria monocytogenes-ivanovii. This method retains the most species-level information. For example, approximately the top 100 most likely matches are returned rather than the top 3 as the reference 16S database can have many highly similar sequences. This scenario occurs particularly often in pathogens, as many similar sequences from related strains are often deposited in databases due to increased study of these organisms.

The method further comprises the use of a well-curated 16S gene database. To enable species level resolution in taxonomy assigned using the way described above, the 16S gene reference database needs to well curated. The regular publicly available databases (e.g. Greengenes, Silva, RDP) are full of erroneous sequences and annotations. If the query 16S amplicon sequence is indeed from Listeria monocytogenes, but the taxonomy of the most likely match is to a sequence erroneously deposited as an unknown genus, the query will be assigned as an unknown genus. In another example, a 16S belonging to *Imtechella halotolerans* was deposited prior to this organism being named as a species and thus was annotated it as *Imtechella sp.* In both cases, the improper taxonomy can be corrected by conducting a nucleotide sequence search (such as BLAST) of the sequence with limited annotation to determine if the same sequence has been deposited with more detailed information. Sequences with high sequence identity but with conflicting annotations are then identified and curated manually. An additional issue with reference sequence databases is that the deposited sequences themselves may not be free of artifact and/or error. Every widely-used method of sequencing has a non-zero rate along with the amplification step which can produce both chimeric sequences and sequence errors. In both cases, failure to properly identify an error or artifact can lead to its misidentification as a new genus, species, or strain. This is particularly prevalent in the case of chimeric sequences, as they can arise from the inappropriate hybridization of partial amplicons from two distinct phyla, genre, or species of bacteria during amplification and result in what appears to be an entirely novel 16S gene sequence. If this error is not detected, the sequence may be deposited as an unknown phylum. When the V3-V4 region of one of the two origin species is partially sequenced, it might have a perfect match to this chimeric sequence in the reference database and result in erroneous taxonomy.

Another problem with common 16S databases is that many sequences in the database belong to microbes that have an unknown species name, with multiple distinct unnamed species being present in a sample. Assignment of microbial names is a long process that requires significant laboratory work to characterize the microbe in question. In order to achieve species-level resolution for amplicon sequences derived from unnamed species, a system is provided that assigns unit species IDs to sequences that previously had unknown species names. 16S sequences with unknown species names are first clustered into groups with 97% identity. Then from each group one is picked as representative based on its occurrence in the database. Then, a unique species name (e.g. sp00001) is assigned to the sequence.

I. 16S Sequencing for Microbial Sample Characterization

Certain embodiments of the present disclosure provide methods for the identification and/or quantification of microbial samples.

The microbial sample is subjected to lysis to isolate nucleic acids for analysis. In particular embodiments, the sample is contacted with a lysis buffer (e.g., containing a buffering agents, chaotropic salts, ionic detergents, non-ionic detergents solvents, EDTA, Trizol, monovalent and divalent salts). In some embodiments, the present disclosure provides appropriate salts (e.g. NaCl, KOH, $MgCl_2$, etc.) and salt concentration (e.g. high salt, low salt, 1 mM, 2 mM, 5 mM, 10 mM, 20 mM, 50 mM, 100 mM, 200 mM, 500 mM, 1 M, 2 M, 3 M, 4 M, 5 M, etc.) for use with the array of sample containers (e.g., a plurality of beads). In some embodiments, buffers for use with the array of sample containers (e.g., a plurality of beads) may include, but are not limited to $H_3PO_4$ / $NaH_2PO_4$, Glycine, Citric acid, Acetic acid, Citric acid, MES, Cacodylic acid, $H_2CO_3$ / $NaHCO_3$, Citric acid, Bis-Tris, ADA, Bis-Tris Propane, PIPES, ACES, Imidazole, BES, MOPS, $NaH_2PO_4$ / $Na_2HPO_4$, TES, HEPES, HEPPSO, Triethanolamine, Tricine, Tris, Glycine amide, Bicine, Glycylglycine, TAPS, Boric acid ($H_3BO_3$ / $Na_2B_4O_7$), CHES, Glycine, $NaHCO_3$ / $Na_2CO_3$, CAPS, Piperidine, $Na_2HPO_4$ / $Na_3PO_4$, and combinations thereof.

As indicated above, DNA such as genomic DNA can be isolated from one or more cells, bodily fluids or tissues. An array of methods can be used to isolate DNA from samples such as surface swabs, blood, sweat, tears, lymph, urine, saliva, semen, cerebrospinal fluid, amniotic fluid, feces, soil, water, sludge, etc. DNA can also be obtained from one or more cell or tissue in primary culture, in a propagated cell line, a fixed archival sample, forensic sample or archeological sample.

The sample may be a "host derived sample" referred to herein as any organism that serves as an environment for microorganisms to reside on whether it resides as a resident or as a transient. Animals and plants frequently serve as such hosts for microorganisms. Methods for isolating genomic DNA from a cell, fluid or tissue are well known in the art (see, e.g., Sambrook et al., 2001). Yeast species (e.g. *Saccharomyces cerevisiae*), fungi species, other microorganisms, human (*Homo sapiens*) liquid tissue (e.g. sputum, lymph fluid, cerebrospinal fluid (CSF), urine, serum, sweat, various aspirates, and other liquid biological sources ) solid tissue, or tissue from a variety of species commonly used in diagnostic, research or clinical laboratories are contemplated as compatible with this purification procedure as sources of DNA and are all alternative embodiments of the present invention.

The bacterial species may comprise gram positive or gram negative strains, such as one or more of the strains *Bacillus subtilis*, *Listeria monocytogenes*, *Staphylococcus aureus*, *Enterococcus faecalis*, *Lactobacillus fermentum*, *Salmonella enterica*, *Escherichia coli*, *Pseudomonas aeruginosa*, *Saccharomyces cerevisiae*, and *Cryptococcus neoformans*. Procedures for handling and preparing samples from these various species are well known in the art and are reported in the scientific literature.

In certain embodiments, the present methods further comprise the purification and analysis of the DNA and/or RNA released from the sample using sheer or compression or tensile forces. The further analysis may comprise, for example, 16S rRNA gene sequencing.

Isolation of DNA and RNA is well known in the art. In particular embodiments, DNA isolation is performed using a commercially available kit such as the ZymoBIOMICS™ DNA Mini Kit. In particular aspects, the isolation is performed free of PCR inhibitors, such as polyphenols, humic and fulvic acids). In exemplary methods, plasmid isolation comprises modified mild alkaline lysis of host cells containing a plasmid, sodium hydroxide (NaOH) and sodium dodecyl sulphate (SDS), NaOH/SDS, denaturation, and precipitation of unwanted cellular macromolecular components as an insoluble precipitate, coupled to column-based silica, or other chromatography or purification methods. Isolation buffers based on alkaline lysis protocols are well known in the art and variations of compositions are contemplated as embodiments of the present invention that are compatible with various commercially available chromatographic columns and technologies. Alkaline lysis procedures generally use sodium acetate, potassium acetate, as well as a variety of other salts, including chaotropic salts. Ribonuclease RNAase A is commonly added to degrade contaminating RNA from the lysate. The clarification of the lysate can be performed by centrifugation or filtration methods both of which are known in the art. The plasmid is pure, typically with an OD260/280 ratio above 1.8. The plasmid DNA is suitably pure for use in the most sensitive experiments.

A number of methods have been used to isolate DNA from samples. For example, U.S. Pat. No. 5,650,506 relates to modified glass fiber membranes which exhibit sufficient hydrophilicity and electropositivity to bind DNA from a suspension containing DNA and permit elution of the DNA from the membrane. The modified glass fiber membranes are useful for purification of DNA from other cellular components. U.S. Pat. Nos. 5,705,628 and 5,898,071 disclose a method for separating polynucleotides, such as DNA, RNA and PNA, from a solution containing polynucleotides by reversibly and non-specifically binding the polynucleotides to a solid surface, such as a magnetic microparticle. A similar approach has been used in a product, "DYNABEADS DNA Direct" marketed by DYNAL A/S, Norway. Similarly, glass, plastic and other types of beads have been used to bind to and isolate DNA from solutions. Commercially, ZymoResearch offers the ZymoBIOMICS™-96 MagBead DNA Kit which includes beads for homogenization of diverse samples.

In some aspects, the nucleic acid is isolated as described by Ruggiere et al. (Springer Protocols Handbooks, Sample Preparation Techniques for Soil, Plant, and Animal Samples, 41-52, 2016; incorporated herein by reference). For example, phase separation techniques utilizing phenol-chloroform or acid guanidinium thiocyanate-phenol-chloroform extraction (e.g., Tri-Reagent® or Trizol® by commercial suppliers MRC and Invitrogen, respectively) and column-based separation techniques (that use a solid phase carrier such as silica or anion exchange resins) are the most prevalent methods used for nucleic acid isolation. Other technologies have also been employed for the binding and purification of nucleic acid including nitrocellulose, polyamide membranes, glass particles (powder or beads), diatomaceous earth, and anion-exchange materials (such as diethylaminoethyl cellulose).

Organic phase extraction of nucleic acids involves adding phenol and chloroform to a sample. The result is the formation of a biphasic emulsion which, upon centrifugation, the organic-hydrophobic solvents containing lipids, proteins, and other cellular components will settle on the bottom of the aqueous layer that contains the nucleic acids (Kirby, 1956; Grassman & Deffner, 1953; Tan & Yiap, 2009). The aqueous phase is subsequently partitioned from the organic layer for use in the precipitation of the nucleic acids. Ethanol (or isopropanol) with ammonium acetate (or some ionic salt) is used to precipitate the nucleic acids from the partitioned aqueous layer (Tan & Yiap, 2009). The nucleic acid is pelleted by centrifugation, washed with ethanol, and then resuspended in the desired low-salt solution (usually water or TE) for use in downstream analysis.

Due to the inherent nature of the chemistry of organic separation, DNA and RNA can be co-purified or selectively isolated individually. To selectively isolate DNA, an RNase A treatment may be necessary to remove RNA present in the aqueous layer (Rogers and Bendich, 1985). For effective DNA isolation, the aqueous layer must have a basic pH. Acidification using acid guanidinium thiocyanate-phenol-chloroform extraction, forces DNA to be partitioned into the interphase and organic phase, allowing for convenient isolation of RNA directly from the aqueous phase (Chomczynski & Sacchi, 1987 and Chomczynski et al., 1989).

In column-based separation, such as silica-based methods, use of a chaotropic agent, such as guanidinium chloride, will cause nucleic acids to selectively (and reversibly) bind to silica particles. The silica-nucleic acid-bound complexes can be subsequently washed with an alcohol solution to remove contaminants and then the nucleic acids eluted using water or TE. Spin-column extractions are well characterized and highly consistent due to reduced handling compared to phenol-chloroform extractions (Price et. al., 2009). They allow for quick and efficient purification by circumventing many of the problems associated with organic-phase separation such as incomplete phase separation and hassle of working with highly toxic solvents (Tan & Yiap, 2009).

A. RNA Purification Method

Several methods are available for the purification of RNA, such as described above. For example, the Zymo Quick-RNA™ MiniPrep Plus kit may be used to purify high-quality total RNA. In addition, Zymo DNA/RNA Shield™ ensures nucleic acid stability during sample storage/transport at ambient temperatures. In one exemplary method, RNA may be purified by the methods described in U.S. Patent No. 9,051,563, incorporated herein by reference. In general, the method comprises (a) obtaining sample comprising a nucleic acid molecule and phenol and (b) contacting the sample to a silica substrate in the presence of a binding agent comprising a chaotropic salt, an alcohol or a combination thereof, thereby binding the nucleic acid molecule to the silica substrate. In certain aspects, a nucleic acid containing sample may comprise a substantial amount of phenol, such as about or greater than about 10%, 20%, 30%, 40% or 50% phenol by volume. A binding agent may comprise an alcohol such as a lower alcohol, e.g., methanol, ethanol, isopropanol, butanol or a combination thereof.

The addition of a chaotropic salt may be used for cell lysis and the formation of an RNA-containing precipitate. The term chaotropic salt refers to a substance capable of altering the secondary or tertiary structure of a protein or nucleic acid, but not altering the primary structure of the protein or nucleic acid. Examples of chaotropic salts include, but are not limited to, guanidine thiocyanate, guanidine hydrochloride sodium iodide, potassium iodide, sodium isothiocyanate, and urea. Guanidine salts other than guanidine thiocyanate and guanidine hydrochloride may be used as a chaotropic salts in the subject methods. Preferred chaotropic salts for use in the present methods are guanidine hydrochloride and guanidine thiocyanate. The concentration of chaotropic salt used to elicit RNA-containing precipitant formation may vary in accordance with the specific chaotropic salt selected. Factors such as the solubility of the specific salt must be taken into account. Routine experimentation may be used in order to determine suitable concentration of chaotropic salt for eliciting RNA-containing precipitate formation. In embodiments of the present methods employing guanidine hydrochloride as the chaotropic salt, the concentration of guanidine hydrochloride in the nucleic acid containing solution from which the RNA-containing precipitate is obtained is in the range of 1 M to 3 M, 2 M being particularly preferred. In embodiments of the present methods employing guanidine thiocyanate as the chaotropic salt, the concentration of guanidine thiocyanate in the nucleic acid-containing solution from which the RNA-containing precipitate is obtained is in the range of 0.5 M to 2 M, 1 M being particularly preferred. Combinations of chaotropic salts may be used to elicit RNA-containing precipitate formation. In embodiments of the invention employing multiple chaotropic salts, the chaotropic salts may be added in the form of concentrated solution or as a solid (and dissolved in the initial RNA-containing preparation).

After the addition of the chaotropic salts, the solution is allowed to incubate for a period of time sufficient to permit an RNA-containing precipitate to form. Unless the incubation conditions are modified during incubation, e.g., a temperature change, the longer the period of incubation time, the larger the quantity of RNA precipitate that will form. Incubation preferably occurs under constant temperature conditions. When a sufficient quantity of RNA precipitate for the purpose of interest, e.g., cDNA library formation, is formed, the RNA precipitate may be collected. The quantity of RNA precipitate formed may be monitored during incubation. Monitoring may be achieved by many methods, such methods include visually observing the formation of the precipitate (e.g., visually), collecting the precipitate during the incubation process and the like. In most embodiments of the invention, incubation time is at least one hour, preferably incubation is at least eight hours. Periods for incubation may be considerably longer than eight hours; no upper limit for incubation time is contemplated although need to obtain isolated RNA in a reasonable amount of time may be a constraint.

The temperature of the mixture formed by adding the chaotropic salt to the RNA-containing composition of interest, e.g., mixed microbial sample, influences the amount of RNA-containing precipitate formed in the subject method. In general, a greater precipitate yield will be obtained at a lower temperature, i.e., below room temperature. Preferably, freezing is avoided; however, a RNA-containing precipitate may form if a fresh cellular lysate is rapidly frozen. Additionally, lower temperatures may be used to reduce the activity of RNAses or detrimental chemical reactions occurring in the processed sample. Preferably, the temperature of the solution from which the RNA-containing precipitate formed is in the range of 1° C. to 25° C., more preferably in the range of 4° C. to 10° C.

After the RNA-containing precipitate has formed, the RNA-containing precipitate is collected. Collection entails the removal of the RNA-containing precipitate from the solution from which the precipitate was formed. The precipitate may be separated from the solution by any of the well-known methods for separation of a solid phase from a liquid phase. For example, the RNA-containing precipitate may be recovered by filtration or centrifugation. Many types of filtration and centrifugation systems may be used to collect the RNA-containing precipitate. Precautions against RNA degradation should be taken during the RNA precipitate collection step, e.g., the use of RNAase-free filters and tubes, reduced temperatures.

After the RNA-containing precipitate has been recovered, the precipitate may optionally be washed so as to remove remaining contaminants. A variety of wash solutions may be used. Wash solutions and washing conditions should be designed so as to minimize RNA losses from the RNA-containing precipitate. Preferably a wash solution containing the same chaotropic salt used to form the RNA-containing precipitate is used to wash the collected RNA-containing precipitate. The concentration of the chaotropic salt in the wash solution is preferably high enough for an RNA-containing precipitate to form, thereby minimizing losses of the RNA-containing precipitate during the washing process. Additionally, the washing solution is preferably at a temperature sufficiently low for RNA-containing precipitates to form, thereby minimizing losses of the RNA-containing precipitate during the washing process.

The collected RNA-containing precipitate may be solubilized so as to enable subsequent manipulation of the purified RNA in solutions. Solubilization may be accomplished by contacting the collected RNA-containing precipitate with a solution that does not elicit the formation of an RNA-containing precipitate. Typically, such a solution is an aqueous buffer (low ionic strength) or water. Examples of such buffers includes 10 mM Tris-HCl (pH 7.0), 0.1 mM EDTA; suitable buffering agents include, but are not limited to, tris, phosphate, acetate, citrate, glycine, pyrophosphate, aminomethyl propanol, and the like. The RNA-containing precipitate and the solution may be actively mixed, e.g., by vortexing, in order to expedite the solubilization process.

B. Magnetic Bead DNA Purification of Nucleic Acids

In some embodiments, the nucleic acids are purified using magnetic microparticles, such as magnetic beads. Silica materials, including glass particles, such as glass powder, silica particles, and glass microfibers prepared by grinding glass fiber filter papers, and including diatomaceous earth, have been employed in combination with aqueous solutions of chaotropic salts to separate nucleic acids from other substances and render the nucleic acids suitable for use in molecular biological procedures (see U.S. Pat. No. 5,075,430; incorporated herein by reference). Such matrices are designed to remain bound to the nucleic acid material while the matrix is exposed to an external force such as centrifugation or vacuum filtration to separate the matrix and nucleic acid material bound thereto from the remaining media components. The nucleic acid material is then eluted from the matrix by exposing the matrix to an elution solution, such as water or an elution buffer. Numerous commercial sources offer silica-based matrices designed for use in centrifugation and/or filtration isolation systems. See, e.g. Wizard™ DNA purification systems line of products from Promega Corporation (Madison, Wis., U.S.A.); or the Qia-Prep™ line of DNA isolation systems from Qiagen Corp. (Chatsworth, Calif., U.S.A.). Exemplary magnetic particle purification methods are disclosed in, for example, U.S. Pat. Nos. 6027945, 6284470, 6673631, and 7078224; each incorporated herein by reference.

A complex of the silica magnetic particles and the DNA target material is formed by exposing the particles to the medium containing the DNA target material under conditions designed to promote the formation of the complex. The complex is preferably formed in a mixture of the silica magnetic particles, the medium, and a chaotropic salt. The complex is removed from the mixture using a magnetic field. Other forms of external force in addition to the magnetic field can also be used to isolate the biological target substance according to the methods of the present invention after the initial removal step. Suitable additional forms of external force include, but are not limited to, gravity filtration, vacuum filtration and centrifugation. The nucleic acid material is eluted from the silica magnetic particle by exposing the complex to an elution solution. The elution solution is preferably an aqueous solution of low ionic strength, more preferably water or a low ionic strength buffer at about a pH at which the nucleic acid material is stable and substantially intact. Any aqueous solution with an ionic strength at or lower than TE buffer (i.e. 10 mM Tris-HCl, 1 mM ethylenediamine-tetraacetic acid (EDTA), pH 8.0) is suitable for use in the elution steps of the present methods, but the elution solution is preferable buffered to a pH between about 6.5 and 8.5, and more preferably buffered to a pH between about 7.0 and 8.0. TE Buffer and distilled or deionized water are particularly preferred elution solutions for use in the present invention. The low ionic strength of the preferred forms of the elution solution described above ensures the nucleic acid material is released from the particle. Other elution solutions suitable for use in the present methods will be readily apparent to one skilled in this art.

Chaotropic salts are salts of chaotropic ions. Such salts are highly soluble in aqueous solutions. The chaotropic ions provided by such salts, at sufficiently high concentration in aqueous solutions of proteins or nucleic acids, cause proteins to unfold, nucleic acids to lose secondary structure or, in the case of double-stranded nucleic acids, melt (i.e., strand-separate). It is thought that chaotropic ions have these effects because they disrupt hydrogen-bonding networks that exists in liquid water and thereby make denatured proteins and nucleic acids thermodynamically more stable than their correctly folded or structured counterparts. Chaotropic ions include guanidinium, iodide, perchlorate and trichloroacetate. Preferred in the present invention is the guanidinium ion. Chaotropic salts include guanidine hydrochloride, guanidine thiocyanate, sodium iodide, sodium perchlorate, and sodium trichloroacetate.

At least two commercial silica magnetic particles are particularly preferred for use in the present disclosure, Bio-Mag® Magnetic Particles from PerSeptive Biosystems, and the MagneSil™ Particles available from Promega Corporation (Madison, Wis.). Any source of magnetic force sufficiently strong to separate the silica magnetic particles from a solution would be suitable for use in the nucleic acid isolation methods of the present invention. However, the magnetic force is preferably provided in the form of a magnetic separation stand, such as one of the MagneSphere® Technology Magnetic Separation Stands (cat. nos. Z5331 to 3, or Z5341 to 3) from Promega Corporation.

When the target nucleic acid is genomic DNA, it is necessary to disrupt the tissue to release the target genomic DNA from association with other material in the tissue, so the target genomic DNA can adhere to the pH dependent ion exchange matrix in the presence of a solution at the first pH. The resulting complex of matrix and genomic DNA is separated from the disrupted tissue, and washed to remove additional contaminants (if necessary). The genomic DNA is then eluted from the complex by combining the complex with an elution solution having a second pH which is higher than the first pH.

Magnetic microparticles useful in the present method can be a variety of shapes, which can be regular or irregular; preferably the shape maximizes the surface areas of the microparticles. The magnetic microparticles should be of such a size that their separation from solution, for example by filtration or magnetic separation, is not difficult. In addition, the magnetic microparticles should not be so large that surface area is minimized or that they are not suitable for microscale operations. Suitable sizes range from about 0.1 μ mean diameter to about 100 μ mean diameter. A preferred size is about 1.0 μ mean diameter. Suitable magnetic microparticles are commercially available from PerSeptive Diagnostics and are referred to as BioMag COOH (Catalog Number 8-4125).

As used herein, the term "magnetic particles" or "magnetic microparticles" refers to materials which have no magnetic field but which form a magnetic dipole when exposed to a magnetic field, i.e., materials capable of being magnetized in the presence of a magnetic field but which are not themselves magnetic in the absence of such a field. The term "magnetic" as used in this context includes materials which are paramagnetic or superparamagnetic materials. The term "magnetic", as used herein, also encompasses temporarily magnetic materials, such as ferromagnetic or ferrimagnetic materials with low Curie temperatures, provided that such temporarily magnetic materials are paramagnetic in the temperature range at which silica magnetic particles containing such materials are used according to the present methods to isolate biological materials.

Salts which have been found to be suitable for binding DNA to the microparticles include sodium chloride (NaCl), lithium chloride (LiCl), barium chloride ($BaCl_2$), potassium (KCl), calcium chloride ($CaCl_2$), magnesium chloride ($MgCl_2$) and cesium chloride (CeCl). In one embodiment sodium chloride is used in the present of PEG or cationic detergents such as CTAB. The wide range of salts suitable for use in the method indicates that many other salts can also be used and can be readily determined by one of ordinary skill in the art. Yields of bound DNA decrease if the salt concentration is adjusted to less than about 0.5 M or greater than about 5.0 M. The salt concentration is preferably adjusted to about 1.25 M.In one embodiment, the magnetic microparticles with bound DNA are washed with a suitable wash buffer solution before separating the DNA from the microparticles by washing with an elution buffer. A suitable wash buffer solution has several characteristics. First, the wash buffer solution must have a sufficiently high salt concentration (i.e., has a sufficiently high ionic strength) that the DNA bound to the magnetic microparticles does not elute off of the microparticles, but remains bound to the microparticles. Suitable salt concentrations are greater than about 1.0 M and is preferably about 5.0 M. Second, the buffer solution is chosen so that impurities that are bound to the DNA or microparticles are dissolved. The pH and solute composition and concentration of the buffer solution can be varied according to the type of impurities which are expected to be present. Suitable wash solutions include the following: 0.5×5 SSC; 100 mM ammonium sulfate, 400 mM Tris pH 9, 25 mM $MgCl_2$ and 1% bovine serum albumine (BSA); and 5 M NaCl. A preferred wash buffer solution comprises 25 mM Tris acetate (pH 7.8), 100 mM potassium acetate (KOAc), 10 mM magnesium acetate ($Mg_2$OAc), and 1 mM dithiothreital (DTT). The magnetic microparticles with bound DNA can also be washed with more than one wash buffer solution. The magnetic microparticles can be washed as often as required to remove the desired impurities. However, the number of washings is preferably limited to two or three in order to minimize loss of yield of the bound DNA. Yields of DNA when the microparticles are used in excess are typically about 80% after washing with a wash buffer and eluting with an elution buffer.

An affordable automated purification device with bead beating integrated onto the device for unbiased nucleic acid extraction by multiple methods can be developed comprising the aforementioned methodologies and the following is an example of a preferred embodiment. The device could utilize bead mover technology as exemplified by the Maxwell® 16 Purification System or KingFisher™Flex Purification System for the purification of nucleic acids from a lysate using chaotropic salts and magnetic silica microparticles. Other chemistries and methods of purification would be apparent to one skilled in the art and could readily be substituted such as but not limited to PEG/Carboxylated Microparticles or PEG/Cellulose Microparticles. The purification would be performed in a cartridge composed of plurality of wells that could be filled with a plurality of components for the nucleic acid isolation and purification including, but not limited to bead beating beads for lysis, magnetic silica beads for purification, bead beating solutions, binding solutions, washing solutions, and elution solutions. In a preferred case, the bead beating solution and binding solution are the same solution. The wells would either be sufficiently deep such that during the bead beating process no cross contamination occurs or a sealing mechanism such as a foil or plunger is used to prevent cross contamination. The sample would be loaded into a well containing the lysis solution and BashingBeads. The bead beating could be performed using an orbital shaker or modified orbital shakers to provide a more chaotic motion which is preferable to increase the number of collisions. The speed at which the unit moves would be between 1,000 RPM and 10,000 RPM. More preferably the speed would be between 2,000 RPM and 5,000 RPM. The most preferred speed would be one in which an unbiased lysis occurs as validated using a mock microbial community standard such as the ZymoBIOMICS Microbial Community Standard which includes a range of organisms of varying recalcitrance to lysis (i.e. yeast, gram-positive bacteria, and gram-negative bacteria). An alternative approach would be that the bead mover executes an agitation motion that causes the bead bashing as opposed to the plate where the cartridge is inserted. A preferred embodiment would be a system where the minimal force is met to lyse cells of plurality of sizes and recalcitrance to lysis wherein "tough-to-lyse" cells as efficiently lysed as the "easy-to-lyse cells" such that reasonably uniform lysis is achieved and the number of collisions per second is sufficient to lyse them in a reasonable period of time (i.e. < 1 hour and more preferably < 20 minutes) at a speed and motion that is achievable in an affordable manner. Following lysis, if binding reagents are already present the bead mover could transfer the binding beads into the well with the lysate and shake gently to facilitate homogenous binding without breaking down the binding beads. A preferred speed for such operations is below 1,000 RPM and more preferably below 500 RPM. If the lysis solution did not contain binding reagents a dispenser such attached to a simple pump such as, but not limited to, a peristaltic pump to dispense a binding reagent. One contemplated embodiment is parallel purification of DNA and RNA from the same sample and in this case, it may be preferable to add alcohol via a separate dispenser unit and have two sets of magnetic binding beads in order to achieve parallel purification of DNA and RNA. Following binding the magnetic beads would be transferred using the bead mover to the next well(s) containing wash buffers where mixing preferably occurs, but is not required, and finally transferred to the elution buffer where mixing preferably occurs but is also not required. Lastly, the magnetic beads are transferred out of the solution so that the users may remove the eluate. In some instances, the final well maybe a tube that can be removed such as a 1.5 ml centrifuge tube.

C. 16S Sequencing

After DNA isolation, the DNA can be selectively PCR-amplified using primers targeting the 16S rRNA gene and processed based on methods known in the art for the specific sequencing platform. During amplification, a quantitative PCR method can be utilized to monitor the amplification efficiency and discontinue the reaction once the reaction efficiency has started to decrease. This modification of the standard PCR-based amplification method minimizes the creation of chimeric sequences that commonly begin to form as the amplification reaction encounters limiting amounts of remaining reactants (often due to consumption of specific deoxynucleotide triphosphates by the reaction itself).

Common next-generation sequencing platforms cover 100-600 base pairs per single read with varying degrees of accuracy, but the full-length 16S rRNA gene consists of approximately 1,500 base pairs. Therefore, primers are chosen to cover only a portion of the 16S rRNA gene. In the present methods, the V1-V2 or V3-V4 regions were selected as the primer regions. In further aspects, nanopore sequencing may be used sequencing of e.g., 16S sequecnes or portions thereof (see, e.g., U.S. Pat. Nos. 10,081,835 and 9,546,400, which are incorporated herein by reference).

The amplified PCR products can then be sequencing using a next-generating sequencing platform, such as Illumina MiSeq, Roche 454, or Ion Torrent. Any high-throughput technique for sequencing can be used in the practice of the invention. DNA sequencing techniques include dideoxy sequencing reactions (Sanger method) using labeled terminators or primers and gel separation in slab or capillary, sequencing by synthesis using reversibly terminated labeled nucleotides, pyrosequencing, 454 sequencing, sequencing by synthesis using allele specific hybridization to a library of labeled clones followed by ligation, real time monitoring of the incorporation of labeled nucleotides during a polymerization step, polony sequencing, SOLID sequencing, and the like.

Certain high-throughput methods of sequencing comprise a step in which individual molecules are spatially isolated on a solid surface where they are sequenced in parallel. Such solid surfaces may include nonporous surfaces (such as in Solexa sequencing, e.g. Bentley et al, Nature, 456: 53-59 (2008) or Complete Genomics sequencing, e.g. Drmanac et al, Science, 327: 78-81 (2010)), arrays of wells, which may include bead- or particle-bound templates (such as with 454, e.g. Margulies et al, Nature, 437: 376-380 (2005) or Ion Torrent sequencing, U.S. Patent Publication 2010/0137143 or 2010/0304982), micromachined membranes (such as with SMRT sequencing, e.g. Eid et al, Science, 323: 133-138 (2009)), or bead arrays (as with SOLiD sequencing or polony sequencing, e.g. Kim et al, Science, 316: 1481-1414 (2007)). Such methods may comprise amplifying the isolated molecules either before or after they are spatially isolated on a solid surface. Prior amplification may comprise emulsion-based amplification, such as emulsion PCR, or rolling circle amplification.

Of particular interest is sequencing on the Illumina® MiSeq platform, which uses reversible-terminator sequencing by synthesis technology (see, e.g., Shen et al. (2012) *BMC Bioinformatics* 13:160; Junemann etal. (2013)*Nat. Biotechnol.* 31(4):294-296; Glenn (2011)*Mol. Ecol. Resour.* 11(5):759-769; Thudi et al. (2012) *Brief Funct. Genomics* 11(1):3-11; herein incorporated by reference).

Once the DNA sequences are obtained, bioinformatics tools may be used for sequence processing, taxonomic assignment, diversity analysis, and community comparisons. A frequently used term in 16S rRNA gene analysis is the operational taxonomic unit (OTU), which is a set of sequences with high similarity/identity (generally greater than 97%) and therefore binned (or categorized) into a single group. Raw next-generation sequencing data are processed to minimize errors and are subjected to two different, but complementary, analysis strategies. One is a reference-based approach, where sequences, or OTUs, are compared and grouped according to their similarity to existing reference sequences.

Determining the strain or species of microbe in a sample can alternatively or additionally comprise comparing nucleic acid sequence data to a database containing correlation data between promoter sequence characteristics described herein and identification of a microbial strain and/or species.

II. Methods of Use

It is contemplated that the methods described herein are useful to study the natural diversity of bacterial species, resolve unclassified isolates into novel species or strains, define regional and global epidemiology of bacterial species, i.e., naturally occurring endemic strains, disease-causing epidemic strains, and strains with the potential to be agents for bioterrorism, study the epidemiology of infectious diseases, differentiate pathogenic organisms, identify bacterial contamination sources (e.g., hospital-acquired/nosocomial, foodborne, animal/zoonosis, environmental), link patient acquisition of a bacterial infection, and track patient-to-patient transmission during infectious disease outbreaks, inform decisions regarding infection prevention and control measures in health care facilities, inform decisions regarding public health response to outbreaks.

Bacteria can be classified on the basis of cell structure, cellular metabolism or on differences in cell components such as DNA, fatty acids, pigments, antigens and quinones. By combining morphology and Gram-staining, most bacteria can be classified as belonging to one of four groups: Gram-positive cocci, Gram-positive bacilli, Gram-negative cocci and Gram-negative bacilli. Bacteria can be aerobic, anaerobic, or facultative anaerobic.

Exemplary bacteria that can be identified using the present methods, include *Acetobacter aurantius, Acinetobacter* species: *Acinetobacter baumannii, Acinetobacter calcoaceticus, Acinetobacter johnsonii, Acinetobacter junii, Acinetobacter lwoffii, Acinetobacter radioresistens, Acinetobacter septicus, Acinetobacter schindleri, Acinetobacter ursingii; Actinomyces* species: *Actinomyces bovis, Actinomyces bowdenii, Actinomyces canis, Actinomyces cardiffensis, Actinomyces catuli, Actinomyces coleocanis, Actinomyces dentalis, Actinomyces denticolens, Actinomyces europaeus, Actinomyces funkei, Actinomyces georgiae, Actinomyces gerencseriae, Actinomyces graevenitzii, Actinomyces hongkongensis, Actinomyces hordeovulneris, Actinomyces howellii, Actinomyces humiferus, Actinomyces hyovaginalis, Actinomyces israelii, Actinomyces marimammalium, Actinomyces meyeri, Actinomyces naeslundii, Actinomyces nasicola, Actinomyces neuii, Actinomyces odontolyticus, Actinomyces oricola, Actinomyces radicidentis, Actinomyces radingae, Actinomyces slackii, Actinomyces streptomycini, Actinomyces suimastitidis, Actinomyces suis, Actinomyces turicensis, Actinomyces urogenitalis, Actinomyces vaccimaxillae, Actinomyces viscosus; Actinobacillus* species: *Actinobacillus actinomycetemcomitans, Actinobacillus arthritidis, Actinobacillus capsulatus, Actinobacillus delphinicola, Actinobacillus equuli, Actinobacillus hominis, Actinobacillus indolicus, Actinobacillus lignieresii, Actinobacillus minor, Actinobacillus muris, Actinobacillus pleuropneumoniae, Actinobacillus porcinus, Actinobacillus rossii, Actinobacillus scotiae, Actinobacillus seminis, Actinobacillus succinogenes, Actinobacillus suis, Actinobacillus ureae; Aeromonas* species: *Aeromonas allosaccharophila, Aeromonas bestiarum, Aeromonas bivalvium, Aeromonas encheleia, Aeromonas enteropelogenes, Aeromonas euchrenophila, Aeromonas hydrophila, Aeromonas ichthiosmia, Aeromonas jandaei, Aeromonas media, Aeromonas molluscorum, Aeromonas popoffii, Aeromonas punctata, Aeromonas salmonicida, Aeromonas schubertii, Aeromonas sharmana, Aeromonas simiae, Aeromonas sobria, Aeromonas veronii; Afipia fells, Agrobacterium* species: *Agrobacterium radiobacter, Agrobacterium rhizogenes, Agrobacterium rubi, Agrobacterium tumefaciens; Agromonas* species, *Alcaligenes* species: *Alcaligenes aquatilis, Alcaligenes eutrophus, Alcaligenes faecalis, Alcaligenes latus, Alcaligenes xylosoxidans; Alishewanella* species, *Alterococcus* species, *Anaplasma phagocytophilum, Anaplasma marginale, Aquamonas* species, *Arcanobacterium haemolyticum, Aranicola* species, *Arsenophonus* species, *Azotivirga* species, *Azotobacter vinelandii, Azotobacter chroococcum, Bacillary dysentery (Shigellosis), Bacillus* species: *Bacillus abortus (Brucella melitensis biovar abortus), Bacillus anthracis (Anthrax), Bacillus brevis, Bacillus cereus, Bacillus coagulans, Bacillus fusiformis, Bacillus globigii, Bacillus licheniformis, Bacillus megaterium, Bacillus mycoides, Bacillus natto, Bacillus stearothermophilus, Bacillus subtilis, Bacillus sphaericus, Bacillus thuringiensis; Bacteroides* species: *Bacteroides forsythus (Tannerella forsythensis), Bacteroides acidifaciens, Bacteroides distasonis (reclassified as Parabacteroides distasonis), Bacteroides gingivalis, Bacteroides gracilis, Bacteroides fragilis, Bacteroides oris, Bacteroides ovatus, Bacteroides putredinis, Bacteroides pyogenes, Bacteroides stercoris, Bacteroides suis, Bacteroides tectus, Bacteroides thetaiotaomicron, Bacteroides vulgatus, Bartonella* species: *Bartonella alsatica, Bartonella bacilliformis, Bartonella birtlesii, Bartonella bovis, Bartonella capreoli, Bartonella clarridgeiae, Bartonella doshiae, Bartonella elizabethae, Bartonella grahamii, Bartonella henselae (cat scratch fever), Bartonella koehlerae, Bartonella muris, Bartonella peromysci, Bartonella quintana, Bartonella rochalimae, Bartonella schoenbuchii, Bartonella talpae, Bartonella taylorii, Bartonella tribocorum, Bartonella vinsonii spp. Arupensis, Bartonella vinsonii spp. Berkhoffii, Bartonella vinsonii spp. Vinsonii, Bartonella washoensis;* BCG (Bacille Calmette-Guerin), *Bergeyella zoohelcum (Weeksella zoohelcum), Bifidobacterium bifidum, Blastobacter* species, *Blochmannia* species, *Bordetella* species: *Bordetella ansorpii, Bordetella avium, Bordetella bronchiseptica, Bordetella hinzii, Bordetella holmesii, Bordetella parapertussis, Bordetella pertussis* (Whooping cough), *Bordetella petrii, Bordetella trematum; Borrelia* species: *Borrelia burgdorferi, Borrelia afzelii, Borrelia anserina, Borrelia garinii, Borrelia valaisiana, Borrelia hermsii, Borrelia Parkeri, Borrelia recurrentis; Bosea* species, *Bradyrhizobium* species, *Brenneria* species, *Brucella* species: *Brucella abortus, Brucella canis, Brucella melitensis, Brucella neotomae, Brucella ovis, Brucella suis, Brucella pinnipediae; Buchnera* species, *Budvicia* species, *Burkholderia* species: *Burkholderia cepacia* (Pseudomonas cepacia), *Burkholderia mallei* (Pseudomonas mallei/ *Actinobacillus mallei*), *Burkholderia pseudomallei* (Pseudomonas pseudomallei); *Buttiauxella* species, *Calymmatobacterium granulomatis, Campylobacter* species: *Campylobacter coli, Campylobacter concisus, Campylobacter curvus, Campylobacter fetus, Campylobacter gracilis, Campylobacter helveticus, Campylobacter hominis, Campylobacter hyointestinalis, Campylobacter insulaenigrae, Campylobacter jejuni, Campylobacter lanienae, Campylobacter lari, Campylobacter mucosalis, Campylobacter rectus, Campylobacter showae, Campylobacter sputorum, Campylobacter upsaliensis; Capnocytophaga canimorsus* (Dysgonic fermenter type 2), *Corynebacterium* species, *Cardiobacterium hominis, Cedecea* species, *Chlamydia* species: *Chlamydia trachomatis* (Lymphogranuloma venereum), *Chlamydia muridarum, Chlamydia suis; Chlamydophila* species: *Chlamydophila pneumoniae, Chlamydophila psittaci* (Psittacosis), *Chlamydophila pecorum, Chlamydophila abortus, Chlamydophila felis, Chlamydophila caviae; Citrobacter* species: *Citrobacter amalonaticus, Citrobacter braakii, Citrobacter farmeri, Citrobacter freundii, Citrobacter gillenii, Citrobacter intermedius, Citrobacter koseri* aka *Citrobacter diversus, Citrobacter murliniae, Citrobacter rodentium, Citrobacter sedlakii, Citrobacter werkmanii, Citrobacter youngae; Clostridium* species: *Clostridium botulinum, Clostridium difficile, Clostridium novyi, Clostridium septicum, Clostridium tetani* (Tetanus), *Clostridium welchii (Clostridium perfringens); Corynebacterium* species: *Corynebacterium diphtheriae* (Diphtheria), *Corynebacterium amycolatum, Corynebacterium aquaticum, Corynebacterium bovis, Corynebacterium equi, Corynebacterium flavescens, Corynebacterium glutamicum, Corynebacterium haemolyticum, Corynebacterium jeikeium* (corynebacteria of group JK), *Corynebacterium minutissimum* (Erythrasma), *Corynebacterium parvum* (also called *Propionibacterium acnes*), *Corynebacterium pseudodiptheriticum* (also called *Corynebacterium hofmannii*),

*Corynebacterium pseudotuberculosis* (also called *Corynebacterium ovis*), *Corynebacterium pyogenes*, *Corynebacterium urealyticum* (corynebacteria of group D2), *Corynebacterium renale*, *Corynebacterium striatum*, *Corynebacterium tenuis* (*Trichomycosis palmellina*, *Trichomycosis axillaris*), *Corynebacterium ulcerans*, *Corynebacterium xerosis*; *Coxiella burnetii* (Q fever), *Cronobacter* species: *Cronobacter sakazakii*, *Cronobacter malonaticus*, *Cronobacter turicensis*, *Cronobacter muytjensii*, *Cronobacter dublinensis*; *Delftia acidovorans* (*Comamonas acidovorans*), *Dickeya* species, *Edwardsiella* species, *Eikenella corrodens*, *Enterobacter* species: *Enterobacter aerogenes*, *Enterobacter cloacae*, *Enterobacter sakazakii*; *Enterococcus* species: *Enterococcus avium*, *Enterococcus durans*, *Enterococcus faecalis* (*Streptococcus faecalis*/*Streptococcus* Group D), *Enterococcus faecium*, *Enterococcus solitarius*, *Enterococcus galllinarum*, *Enterococcus maloratus*; *Ehrlichia chaffeensis*, *Erysipelothrix rhusiopathiae*, *Erwinia* species, *Escherichia* species: *Escherichia adecarboxylata*, *Escherichia albertii*, *Escherichia blattae*, *Escherichia coli*, *Escherichia fergusonii*, *Escherichia hermannii*, *Escherichia vulneris*; *Ewingella* species, *Flavobacterium* species: *Flavobacterium aquatile*, *Flavobacterium branchiophilum*, *Flavobacterium columnare*, *Flavobacterium flevense*, *Flavobacterium gondwanense*, *Flavobacterium hydatis*, *Flavobacterium johnsoniae*, *Flavobacterium pectinovorum*, *Flavobacterium psychrophilum*, *Flavobacterium saccharophilum*, *Flavobacterium salegens*, *Flavobacterium scophthalmum*, *Flavobacterium succinans*; *Francisella tularensis* (Tularaemia), *Francisella novicida*, *Francisella philomiragia*, *Fusobacterium* species: *Fusobacterium necrophorum* (Lemierre syndrome/*Sphaerophorus necrophorus*), *Fusobacterium nucleatum*, *Fusobacterium polymorphum*, *Fusobacterium novum*, *Fusobacterium mortiferum*, *Fusobacterium varium*; *Gardnerella vaginalis*, *Gemella haemolysans*, *Gemella morbillorum* (*Streptococcus morbillorum*), *Grimontella* species, *Haemophilus* species: *Haemophilus aegyptius* (Koch-Weeks bacillus), *Haemophilus aphrophilus*, *Haemophilus avium*, *Haemophilus ducreyi* (Chancroid), *Haemophilus felis*, *Haemophilus haemolyticus*, *Haemophilus influenzae* (Pfeiffer bacillus), *Haemophilus paracuniculus*, *Haemophilus parahaemolyticus*, *Haemophilus parainfluenzae*, *Haemophilus paraphrophilus* (*Aggregatibacter aphrophilus*), *Haemophilus pertussis*, *Haemophilus pittmaniae*, *Haemophilus somnus*, *Haemophilus vaginalis*; *Hafnia* species, *Hafnia alvei*, *Helicobacter* species: *Helicobacter acinonychis*, *Helicobacter anseris*, *Helicobacter aurati*, *Helicobacter bilis*, *Helicobacter bizzozeronii*, *Helicobacter brantae*, *Helicobacter Canadensis*, *Helicobacter canis*, *Helicobacter cholecystus*, *Helicobacter cinaedi*, *Helicobacter cynogastricus*, *Helicobacter felis*, *Helicobacter fennelliae*, *Helicobacter ganmani*, *Helicobacter heilmannii* (*Gastrospirillum hominis*), *Helicobacter hepaticus*, *Helicobacter mesocricetorum*, *Helicobacter marmotae*, *Helicobacter muridarum*, *Helicobacter mustelae*, *Helicobacter pametensis*, *Helicobacter pullorum*, *Helicobacter pylori* (stomach ulcer), *Helicobacter rappini*, *Helicobacter rodentium*, *Helicobacter salomonis*, *Helicobacter trogontum*, *Helicobacter typhlonius*, *Helicobacter winghamensis*; Human granulocytic ehrlichiosis (*Anaplasma phagocytophilum*/*Ehrlichia phagocytophila*), Human monocytotropic ehrlichiosis (Monocytic ehrlichiosis/*Ehrlichia chaffeensis*), *Klebsiella* species: *Klebsiella granulomatis* (*Calymmatobacterium granulomatis*), *Klebsiella mobilis*, *Klebsiella ornithinolytica*, *Klebsiella oxytoca*, *Klebsiella ozaenae*, *Klebsiella planticola*, *Klebsiella pneumoniae*, *Klebsiella rhinoscleromatis*, *Klebsiella singaporensis*, *Klebsiella terrigena*, *Klebsiella trevisanii*, *Klebsiella variicola*; *Kingella kingae*, *Kluyvera* species, *Lactobacillus* species: *Lactobacillus acetotolerans*, *Lactobacillus acidifarinae*, *Lactobacillus acidipiscis*, *Lactobacillus acidophilus* (Doderlein bacillus), *Lactobacillus agilis*, *Lactobacillus algidus*, *Lactobacillus alimentarius*, *Lactobacillus amylolyticus*, *Lactobacillus amylophilus*, *Lactobacillus amylotrophicus*, *Lactobacillus amylovorus*, *Lactobacillus animalis*, *Lactobacillus antri*, *Lactobacillus apodemi*, *Lactobacillus aviarius*, *Lactobacillus bifermentans*, *Lactobacillus brevis*, *Lactobacillus buchneri*, *Lactobacillus camelliae*, *Lactobacillus casei*, *Lactobacillus catenaformis*, *Lactobacillus ceti*, *Lactobacillus coleohominis*, *Lactobacillus collinoides*, *Lactobacillus composti*, *Lactobacillus concavus*, *Lactobacillus coryniformis*, *Lactobacillus crispatus*, *Lactobacillus crustorum*, *Lactobacillus curvatus*, *Lactobacillus delbrueckii*, *Lactobacillus delbrueckii* subsp. *Bulgaricus*, *Lactobacillus delbrueckii* subsp. *Lactis*, *Lactobacillus diolivorans*, *Lactobacillus equi*, *Lactobacillus equigenerosi*, *Lactobacillus farraginis*, *Lactobacillus farciminis*, *Lactobacillus fermentum*, *Lactobacillus formicalis*, *Lactobacillus fructivorans*, *Lactobacillus frumenti*, *Lactobacillus fuchuensis*, *Lactobacillus gallinarum*, *Lactobacillus gasseri*, *Lactobacillus gastricus*, *Lactobacillus ghanensis*, *Lactobacillus graminis*, *Lactobacillus hammesii*, *Lactobacillus hamsteri*, *Lactobacillus harbinensis*, *Lactobacillus hayakitensis*, *Lactobacillus helveticus*, *Lactobacillus hilgardii*, *Lactobacillus homohiochii*, *Lactobacillus iners*, *Lactobacillus ingluviei*, *Lactobacillus intestinalis*, *Lactobacillus jensenii*, *Lactobacillus johnsonii*, *Lactobacillus kalixensis*, *Lactobacillus kefuranofaciens*, *Lactobacillus kefiri*, *Lactobacillus kimchii*, *Lactobacillus kitasatonis*, *Lactobacillus kunkeei*, *Lactobacillus leichmannii*, *Lactobacillus lindneri*, *Lactobacillus malefermentans*, *Lactobacillus mali*, *Lactobacillus manihotivorans*, *Lactobacillus mindensis*, *Lactobacillus mucosae*, *Lactobacillus murinus*, *Lactobacillus nagelii*, *Lactobacillus namurensis*, *Lactobacillus nantensis*, *Lactobacillus oligofermentans*, *Lactobacillus oris*, *Lactobacillus panis*, *Lactobacillus pantheris*, *Lactobacillus parabrevis*, *Lactobacillus parabuchneri*, *Lactobacillus paracollinoides*, *Lactobacillus parafarraginis*, *Lactobacillus parakefiri*, *Lactobacillus paralimentarius*, *Lactobacillus paraplantarum*, *Lactobacillus pentosus*, *Lactobacillus perolens*, *Lactobacillus plantarum*, *Lactobacillus pontis*, *Lactobacillus psittaci*, *Lactobacillus rennini*, *Lactobacillus reuteri*, *Lactobacillus rhamnosus*, *Lactobacillus rimae*, *Lactobacillus rogosae*, *Lactobacillus rossiae*, *Lactobacillus ruminis*, *Lactobacillus saerimneri*, *Lactobacillus sakei*, *Lactobacillus salivarius*, *Lactobacillus sanfranciscensis*, *Lactobacillus satsumensis*, *Lactobacillus secaliphilus*, *Lactobacillus sharpeae*, *Lactobacillus siliginis*, *Lactobacillus spicheri*, *Lactobacillus suebicus*, *Lactobacillus thailandensis*, *Lactobacillus ultunensis*, *Lactobacillus vaccinostercus*, *Lactobacillus vaginalis*, *Lactobacillus versmoldensis*, *Lactobacillus vini*, *Lactobacillus vitulinus*, *Lactobacillus zeae*, *Lactobacillus zymae*; *Leclercia* species, *Legionella* species: *Legionella adelaidensis*, *Legionella anisa*, *Legionella beliardensis*, *Legionella birminghamensis*, *Legionella bozemanii*, *Legionella brunensis*, *Legionella busanensis*, *Legionella cherrii*, *Legionella cincinnatiensis*, *Legionella donaldsonii*, *Legionella drancourtii*, *Legionella drozanskii*, *Legionella erythra*, *Legionella fairfieldensis*, *Legionella fallonii*, *Legionella feeleii*, *Legionella geestiana*, *Legionella genomospecies*, *Legionella gratiana*, *Legionella gresilensis*, *Legionella hackeliae*, *Legionella impletisoli*, *Legionella israelensis*, *Legionella jamestowniensis*, 'Candidatus Legionella jeonii',Legionella jordanis, Legionella lansingensis, Legionella londiniensis, Legionella longbeachae, Legionella lytica, Legionella maceachernii, Legionella micdadei, Legionella moravica, Legionella nautarum, Legionella oakridgensis, Legionella parisiensis, Legionella pneumophila, Legionella quateirensis, Legionella quinlivanii, Legionella rowbothamii, Legionella rubrilucens, Legionella sainthelensi, Legionella santicrucis, Legionella shakespearei, Legionella spiritensis, Legionella steigerwaltii, Legionella taurinensis, Legionella tucsonensis, Legionella wadsworthii, Legionella waltersii, Legionella worsleiensis, Legionella yabuuchiae; Leminorella species, Leptospira species: Leptospira interrogans, Leptospira kirschneri, Leptospira noguchii, Leptospira alexanderi, Leptospira weilii, Leptospira genomospecies 1, Leptospira borgpetersenii, Leptospira santarosai, Leptospira inadai, Leptospira fainei, Leptospira broomii, Leptospira licerasiae, Leptospira biflexa, Leptospira meyeri, Leptospira wolbachii, Leptospira genomospecies 3, Leptospira genomospecies 4, Leptospira genomospecies 5; Lepromatous leprosy (Danielssen-Boeck disease), Leptospira canicola, Leptospira hebdomadis, Leptospirosis (Weil disease/Leptospira icterohaemorrhagiae/Leptospira interrogans serovar icterohaemorrhagiae), Leptotrichia, Leuconostoc species: Leuconostoc carnosum, Leuconostoc citreum, Leuconostoc durionis, Leuconostoc fallax, Leuconostoc ficulneum, Leuconostoc fructosum, Leuconostoc garlicum, Leuconostoc gasicomitatum, Leuconostoc gelidum, Leuconostoc inhae, Leuconostoc kimchii, Leuconostoc lactis, Leuconostoc mesenteroides, Leuconostoc pseudoficulneum, Leuconostoc pseudomesenteroides; Listeria species: Listeria grayi, Listeria innocua, Listeria ivanovii, Listeria monocytogenes (Listeriosis), Listeria seeligeri, Listeria welshimeri; Methanobacterium extroquens, Microbacterium multiforme, Micrococcus species: Micrococcus antarcticus, Micrococcus flavus, Micrococcus luteus, Micrococcus lylae, Micrococcus mucilaginosis, Micrococcus roseus, Micrococcus sedentarius; Mobiluncus, Moellerella species, Morganella species, Moraxella species: Moraxella atlantae, Moraxella boevrei, Moraxella bovis, Moraxella canis, Moraxella caprae, Moraxella catarrhalis (Branhamella catarrhalis), Moraxella caviae, Moraxella cuniculi, Moraxella equi, Moraxella lacunata, Moraxella lincolnii, Moraxella nonliquefaciens, Moraxella oblonga, Moraxella osloensis, Moraxella saccharolytica; Morganella morganii, Mycobacterium species: Mycobacterium abscessus, Mycobacterium africanum, Mycobacterium agri, Mycobacterium aichiense, Mycobacterium alvei, Mycobacterium arupense, Mycobacterium asiaticum, Mycobacterium aubagnense, Mycobacterium aurum, Mycobacterium austroafricanum, Mycobacterium avium (Battey disease/Lady Windermere syndrome), Mycobacterium avium paratuberculosis (implicated in Crohn's disease in humans and Johne's disease in sheep), Mycobacterium avium silvaticum, Mycobacterium avium "hominissuis", Mycobacterium colombiense, Mycobacterium boenickei, Mycobacterium bohemicum, Mycobacterium bolletii, Mycobacterium botniense, Mycobacterium bovis (Bovine tuberculosis), Mycobacterium branderi, Mycobacterium brisbanense, Mycobacterium brumae, Mycobacterium canariasense, Mycobacterium caprae, Mycobacterium celatum, Mycobacterium chelonae, Mycobacterium chimaera, Mycobacterium chitae, Mycobacterium chlorophenolicum, Mycobacterium chubuense, Mycobacterium conceptionense, Mycobacterium confluentis, Mycobacterium conspicuum, Mycobacterium cookii, Mycobacterium cosmeticum, Mycobacterium diernhoferi, Mycobacterium doricum, Mycobacterium duvalii, Mycobacterium elephantis, Mycobacterium fallax, Mycobacterium farcinogenes, Mycobacterium flavescens, Mycobacterium florentinum, Mycobacterium fluoroanthenivorans, Mycobacterium fortuitum, Mycobacterium fortuitum subsp. Acetamidolyticum, Mycobacterium frederiksbergense, Mycobacterium gadium, Mycobacterium gastri, Mycobacterium genavense, Mycobacterium gilvum, Mycobacterium goodii, Mycobacterium gordonae (Mycobacterium aquae), Mycobacterium haemophilum, Mycobacterium hassiacum, Mycobacterium heckeshornense, Mycobacterium heidelbergense, Mycobacterium hiberniae, Mycobacterium hodleri, Mycobacterium holsaticum, Mycobacterium houstonense, Mycobacterium immunogenum, Mycobacterium interjectum, Mycobacterium species: Neisseria gonorrhoea (Gonococcus/Gonorrhea), Neisseria meningiditis (Meningococcus), Neisseria sicca, Neisseria cinerea, Neisseria elongata, Neisseria flavescens, Neisseria lactamica, Neisseria mucosa, Neisseria polysaccharea, Neisseria subflava; Nitrobacter species, Nocardia species: Nocardia asteroides, Nocardia brasiliensis, Nocardia caviae; Noma (cancrum oris/gangrenous stomatitis), Obesumbacterium, Oligotropha species, Orientia tsutsugamushi (Scrub typhus), Oxalobacter formigenes, Pantoea species: Pantoea agglomerans, Pantoea ananatis, Pantoea citrea, Pantoea dispersa, Pantoea punctata, Pantoea stewartii, Pantoea terrea; Pasteurella species: Pasteurella aerogenes, Pasteurella anatis, Pasteurella avium, Pasteurella bettyae, Pasteurella caballi, Pasteurella canis, Pasteurella dagmatis, Pasteurella gallicida, Pasteurella gallinarum, Pasteurella granulomatis, Pasteurella langaaensis, Pasteurella lymphangitidis, Pasteurella mairii, Pasteurella multocida, Pasteurella pneumotropica, Pasteurella skyensis, Pasteurella stomatis, Pasteurella testudinis, Pasteurella trehalosi, Pasteurella tularensis, Pasteurella ureae, Pasteurella volantium; Pediococcus species: Pediococcus acidilactici, Pediococcus cellicola, Pediococcus claussenii, Pediococcus damnosus, Pediococcus dextrinicus, Pediococcus ethanolidurans, Pediococcus inopinatus, Pediococcus parvulus, Pediococcus pentosaceus, Pediococcus stilesii; Peptostreptococcus species: Peptostreptococcus anaerobius, Peptostreptococcus asaccharolyticus, Peptostreptococcus harei, Peptostreptococcus hydrogenalis, Peptostreptococcus indoliticus, Peptostreptococcus ivorii, Peptostreptococcus lacrimalis, Peptostreptococcus lactolyticus, Peptostreptococcus magnus, Peptostreptococcus micros, Peptostreptococcus octavius, Peptostreptococcus prevotii, Peptostreptococcus tetradius, Peptostreptococcus vaginalis; Photorhabdus species, Photorhizobium species, Plesiomonas shigelloides, Porphyromonas gingivalis, Pragia species, Prevotella, Propionibacterium species: Propionibacterium acnes, Propionibacterium propionicus; Proteus species: Proteus mirabilis, Proteus morganii, Proteus penneri, Proteus rettgeri, Proteus vulgaris; Providencia species: Providencia friedericiana, Providencia stuartii; Pseudomonas species: Pseudomonas aeruginosa, Pseudomonas alcaligenes, Pseudomonas anguilliseptica, Pseudomonas argentinensis, Pseudomonas borbori, Pseudomonas citronellolis, Pseudomonas flavescens, Pseudomonas mendocina, Pseudomonas nitroreducens, Pseudomonas oleovorans, Pseudomonas pseudoalcaligenes, Pseudomonas resinovorans, Pseudomonas straminea, Pseudomonas aurantiaca, Pseudomonas aureofaciens, Pseudomonas chlororaphis, Pseudomonas fragi, Pseudomonas lundensis, Pseudomonas taetrolens, Pseudomonas Antarctica, Pseudomonas azotoformans, Pseudomonas brassicacearum, Pseudomonas brenneri, Pseudomonas cedrina, Pseudomonas corrugate, Pseudomonas fluorescens, Pseudomonas gessardii, Pseudomonas libanensis, Pseudomonas mandelii, Pseudomonas marginalis, Pseudomonas mediterranea, Pseudomonas meridiana, Pseudomonas migulae, Pseudomonas mucidolens, Pseudomonas orientalis, Pseudomonas panacis, Pseudomonas proteolytica, Pseudomonas rhodesiae, Pseudomonas synxantha, Pseudomonas thivervalensis, Pseudomonas tolaasii, Pseudomonas veronii, Pseudomonas denitrificans, Pseudomonas pertucinogena, Pseudomonas cremoricolorata, Pseudomonas fulva, Pseudomonas monteilii, Pseudomonas mosselii, Pseudomonas oryzihabitans, Pseudomonas parafulva, Pseudomonas plecoglossicida, Pseudomonas putida, Pseudomonas balearica, Pseudomonas luteola, Pseudomonas stutzeri, Pseudomonas amygdale, Pseudomonas avellanae, Pseudomonas caricapapayae, Pseudomonas cichorii, Pseudomonas coronafaciens, Pseudomonas ficuserectae, Pseudomonas meliae, Pseudomonas savastanoi, Pseudomonas syringae, Pseudomonas viridiflava, Pseudomonas abietaniphila, Pseudomonas acidophila, Pseudomonas agarici, Pseudomonas alcaliphila, Pseudomonas alkanolytica, Pseudomonas amyloderamosa, Pseudomonas asplenii, Pseudomonas azotifigens, Pseudomonas cannabina, Pseudomonas coenobios, Pseudomonas congelans, Pseudomonas costantinii, Pseudomonas cruciviae, Pseudomonas delhiensis, Pseudomonas excibis, Pseudomonas extremorientalis, Pseudomonas frederiksbergensis, Pseudomonas fuscovaginae, Pseudomonas gelidicola, Pseudomonas grimontii, Pseudomonas indica, Pseudomonas jessenii, Pseudomonas jinjuensis, Pseudomonas kilonensis, Pseudomonas knackmussii, Pseudomonas koreensis, Pseudomonas lini, Pseudomonas lutea, Pseudomonas moraviensis, Pseudomonas otitidis, Pseudomonas pachastrellae, Pseudomonas palleroniana, Pseudomonas papaveris, Pseudomonas peli, Pseudomonas perolens, Pseudomonas poae, Pseudomonas pohangensis, Pseudomonas psychrophila, Pseudomonas psychrotolerans, Pseudomonas rathonis, Pseudomonas reptilivora, Pseudomonas resiniphila, Pseudomonas rhizosphaerae, Pseudomonas rubescens, Pseudomonas salomonii, Pseudomonas segitis, Pseudomonas septica, Pseudomonas simiae, Pseudomonas suis, Pseudomonas thermotolerans, Pseudomonas tremae, Pseudomonas trivialis, Pseudomonas turbinellae, Pseudomonas tuticorinensis, Pseudomonas umsongensis, Pseudomonas vancouverensis, Pseudomonas vranovensis, Pseudomonas xanthomarina; Rahnella species, Ralstonia species: Ralstonia basilensis, Ralstonia campinensis, Ralstonia eutropha, Ralstonia gilardii, Ralstonia insidiosa, Ralstonia mannitolilytica, Ralstonia metallidurans, Ralstonia paucula, Ralstonia pickettii, Ralstonia respiraculi, Ralstonia solanacearum, Ralstonia syzygii, Ralstonia taiwanensis; Raoultella species, Rhodoblastus species, Rhodopseudomonas species, Rhinoscleroma, Rhizobium radiobacter, Rhodococcus equi, Rickettsia species: Rickettsia africae, Rickettsia akari, Rickettsia australis, Rickettsia conorii, Rickettsia felis, Rickettsia japonica, Rickettsia mooseri, Rickettsia prowazekii (Typhus fever), Rickettsia rickettsii, Rickettsia siberica, Rickettsia typhi, Rickettsia conorii, Rickettsia africae, Rickettsia psittaci, Rickettsia quintana, Rickettsia rickettsii, Rickettsia trachomae; Rothia dentocariosa, Salmonella species: Salmonella arizonae, Salmonella Bongori, Salmonella enterica, Salmonella enteriditis, Salmonella paratyphi, Salmonella typhi (Typhoid fever), Salmonella typhimurium, Salmonella salamae, Salmonella arizonae, Salmonella diarizonae, Salmonella houtenae, Salmonella indica; Samsonia species, Serratia species: Serratia entomophila, Serratia ficaria, Serratia fonticola, Serratia grimesii, Serratia liquefaciens, Serratia marcescens, Serratia odoriferae, Serratia plymuthica, Serratia proteamaculans, Serratia quinivorans, Serratia rubidaea, Serratia ureilytica; Shewanella putrefaciens, Shigella boydii, Shigella dysenteriae, Shigella flexneri, Shigella sonnei, Sodalis species, Spirillum species: Spirillum minus rat bite fever, Staphylococcus species: Staphylococcus aureus, Staphylococcus auricularis, Staphylococcus capitis, Staphylococcus caprae, Staphylococcus cohnii, Staphylococcus epidermidis, Staphylococcus felis, Staphylococcus haemolyticus, Staphylococcus hominis, Staphylococcus intermedius, Staphylococcus lugdunensis, Staphylococcus pettenkoferi, Staphylococcus saprophyticus, Staphylococcus schleiferi, Staphylococcus simulans, Staphylococcus vitulus, Staphylococcus warneri, Staphylococcus xylosus; Stenotrophomonas species: Stenotrophomonas acidaminiphila, Stenotrophomonas dokdonensis, Stenotrophomonas koreensis, Stenotrophomonas maltophilia, Stenotrophomonas nitritireducens, Stenotrophomonas rhizophila; Streptobacillus species: Streptobacillus moniliformis (Streptobacillary rat bite fever); Streptococcus species: Streptococcus Group A, Streptococcus Group B, Streptococcus agalactiae, Streptococcus aginosus, Streptococcus avium, Streptococcus bovis, Streptococcus canis, Streptococcus cricetus, Streptococcus faceium, Streptococcus faecalis, Streptococcus ferus, Streptococcus gallinarum, Streptococcus lactis, Streptococcus milleri, Streptococcus mitior, Streptococcus mitis, Streptococcus mutans, Streptococcus oralis, Streptococcus peroris, Streptococcus pneumoniae, Streptococcus pyogenes, Streptococcus ratti, Streptococcus salivarius, Streptococcus sanguinis, Streptococcus sobrinus, Streptococcus parasanguinis, Streptococcus suis, Streptococcus thermophilus, Streptococcus vestibularis, Streptococcus viridans, Streptococcus uberis, Streptococcus zooepidemicus; Tatumella species, Trabulsiella species, Treponema species: Treponema carateum (Pinta), Treponema denticola, Treponema endemicum (Bejel), Treponema pallidum (Syphilis), Treponema pertenue (Yaws); Tropheryma whipplei (Whipple disease), Tuberculoid leprosy, Ureaplasma urealyticum, Veillonella, Vibrio species: Vibrio aerogenes, Vibrio aestuarianus, Vibrio agarivorans, Vibrio albensis, Vibrio alginolyticus, Vibrio brasiliensis, Vibrio calviensis, Vibrio campbellii, Vibrio chagasii, Vibrio cholerae (Cholera), Vibrio cincinnatiensis, Vibrio Comma, Vibrio coralliilyticus, Vibrio crassostreae, Vibrio cyclitrophicus, Vibrio diabolicus, Vibrio diazotrophicus, Vibrio ezurae, Vibrio fischeri, Vibrio fluvialis, Vibrio fortis, Vibrio furnissii, Vibrio gallicus, Vibrio gazogenes, Vibrio gigantis, Vibrio halioticoli, Vibrio harveyi, Vibrio hepatarius, Vibrio hispanicus, Vibrio ichthyoenteri, Vibrio kanaloae, Vibrio lentus, Vibrio litoralis, Vibrio logei, Vibrio mediterranei, Vibrio metschnikovii, Vibrio mimicus, Vibrio mytili, Vibrio natriegens, Vibrio navarrensis, Vibrio neonatus, Vibrio neptunius, Vibrio nereis, Vibrio nigripulchritudo, Vibrio ordalii, Vibrio orientalis, Vibrio pacinii, Vibrio parahaemolyticus, Vibrio pectenicida, Vibrio penaeicida, Vibrio pomeroyi, Vibrio ponticus, Vibrio proteolyticus, Vibrio rotiferianus, Vibrio ruber, Vibrio rumoiensis, Vibrio salmonicida, Vibrio scophthalmi, Vibrio splendidus, Vibrio superstes, Vibrio tapetis, Vibrio tasmaniensis, Vibrio tubiashii, Vibrio vulnificus, Vibrio wodanis, Vibrio xuii; Vogesella indigofera, Wigglesworthia species, Wolbachia species, Xenorhabdus species, Yersinia enterocolitica, Yersinia pestis, Yersinia pseudotuberculosis, and Yokenella species.

Common foodbourne bacteria include, but are not limited to Aeromonas hydrophilia, Bacillus cereus, Campylobacter jejuni, Clostridium botulinum, Clostridium perfringens, enteropathogenic *Escherichinia coli* such as O157:H7 (E Coli), *Listeria monocytogenes, Salmonella, Shigella, Staphylococcus aureus, Vibrio* (e.g., *parahaemolyticus*) and *Yersinia enterocolitica.*

III. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1 - 16S Sequencing for Microbial Sample Characterization

To demonstrate the ability of the present methods to achieve strain level resolution, the present bioinformatics pipeline was compared with the Qiime pipeline on three different 16S sequencing datasets: (1) 16S sequencing data from the ZymoBIOMICS Microbial Community Standard, (2) 16S sequencing data from a 16S plasmid standard that contains the full 16S gene of 20 common gut microbes, (3) 16S sequencing data of three real fecal samples.

16S sequencing data of the ZymoBIOMICS Microbial Community Standard: In this example, DNA from the ZymoBIOMICS Microbial Community Standard was extracted using the ZymoBIOMICS DNA Miniprep kit. 16S library preparation was performed using the Quick-16S NGS Library Prep kit with primers targeting 16S V1-V2 regions. Unique sequences from the raw sequencing data was inferred with DADA2. In one way, taxonomy assignment was performed using the Qiime pipeline with Uclust and using GreenGenes database as the reference database. For comparison, the taxonomy was assigned using the present customized script and using an internal 16S database as reference.

Figure 1:
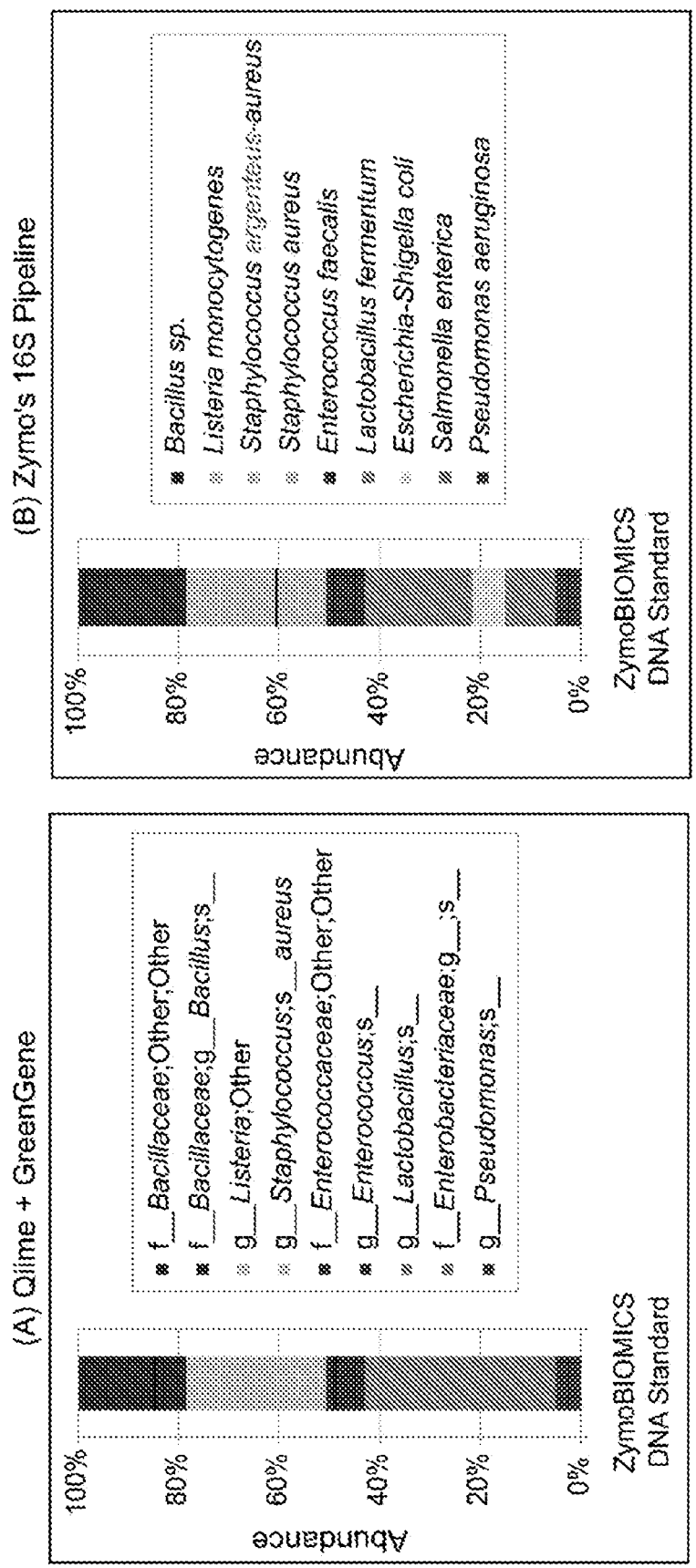
FIG. 1: Comparison of Zymo Research's 16S pipeline with Qiime v.1.9.1 with 16S sequencing data derived from the ZymoBIOMICS Microbial Community Standard. By default, Qiime v.1.9.1 uses the GreenGenes 16S database as the reference database.

The ZymoBIOMICS Microbial Community standard has eight bacteria strains. The primers used in library preparation are able to amplify all of them. The Zymo Research 16S pipeline (part B, FIG. 1) was able to identify 7 of the 8 microbes to the correct species. The organism of Bacillus subtilis was only identified to the genus level because there are more than 3 different Bacillus species including subtilis that were found to share the same sequence in the amplified 16S region. In contrast, the Qiime pipeline, which was used commonly in the microbiomics field, only identified the microbes to genus or family level except for *Staphylococcus aureus.*

16S sequencing data from a 16S plasmid standard that contains the full 16S gene of 20 common gut microbes: In this example, DNA from a plasmid standard was used. This plasmid in the standard contain inserts of complete 16S sequences from 20 microbes commonly found in human gut. The 16S library preparation process was performed with the Quick-16S NGS Library Prep Kit with primers amplifying the 16S V3-V4 region. Bioinformatics analysis was performed in the same way as described in the first example. The Zymo Research 16S pipeline identified all containing microbes to the right species if species is well defined, while the Qiime pipeline only identified 6 out of 20 microbes to species level.

TABLE 1

Analysis of a mock microbial community mimicking human gut with Zymo Research's 16S pipeline as compared to the Qiime Pipeline

| Phylum | Species | Zymo Research | Qiime + GreenGenes |
|---|---|---|---|
| *Euryarchaeoto* | *Methanobrevibacter smithii* | √ | × |
| *Actinobacteria* | *Bifidobacterium adolescentis* | √ | √ |
| *Actinobacteria* | *Bifidobacterium angulatum* | √ | × |
| *Actinobacteria* | *Bifidobacterium ruminantium* | √ | × |
| *Actinobacteria* | *Collinsella aerofaciens* | √ | √ |
| *Bacteroidetes* | *Bacteroides fragilis* | √ | √ |
| *Bacteroidetes* | *Prevotella copri* | √ | √ |
| *Bacteroidetes* | *Sphingobacteriaceae sp.* | √ | × |
| *Firmicutes* | *Catenibacterium mitsuokai* | √ | × |
| *Firmicutes* | *Clostridium difficile* | √ | × |
| *Firmicutes* | *Dialister invisus* | √ | × |
| *Firmicutes* | *Eubacterium rectale* | √ | × |
| *Firmicutes* | *Lactobacillus fermentum* | √ | × |
| *Fusobacteria* | *Fusobacterium nucleatum* | √ | × |
| *Lentisphaerae* | *Victivallis vadensis* | √ | × |
| *Proteobacteria* | *Bilophila wadsworthia* | √ | × |
| *Proteobacteria* | *Escherichia coli* | √ | × |
| *Proteobacteria* | *Sutterella wadsworthensis* | √ | × |
| *Synergistetes* | *Pyramidobacter piscolens* | √ | √ |
| *Verrucomicrobia* | *Akkermansia muciniphila* | √ | √ |

Profiling previously unknown species in fecal samples: The Zymo Research 16S bioinformatics pipeline together with the present 16S database enabled species-level resolution even to previously unknown species. To demonstrate this, 10 fecal samples from 10 different individuals were profiled using 16S sequencing targeting v3-v4 region.

The family of Lachnospiraceae is very abundant in the human gut. In the 10 fecal samples profiled, the average abundance of this family is 32.0%. Common Lachnospiraceae genera found in human gut include *Blautia, Butyrivibrio, Coprococcus, Dorea, Eubacterium, Fusicatenibacter, Lachnoclostridium, Lachnospira, Pseudobutyrivibrio,* and *Roseburia.* However, there are normally a big proportion of sequences from this family are assigned as unknown genus. In the 10 samples profiled (Table 1), these sequences take up from 2.8%-15.1% with an average of 8.0%. In the regular analysis using pipelines like QIIME, this is the most information that can be obtained as they are limited to genus-level resolution. However, with the present pipeline, the potential species can be seen that were assigned to this group of unknown Lachnospiraceae genera (Table 2).

Within this group, there are some species that are frequently found in the ten samples (Table 3). The most similar species among the five species are sp32519 and sp32277. The sequence identity between the reference sequences of these two species is 88%; their sequence identity in the sequenced region, i.e. V3-V4 region, is 95%. The Zymo Research 16S pipeline used DADA2 to infer unique sequences from amplicon sequencing and DADA2 was able to differentiate even single nucleotide differences in the 16S sequencing data. Being able to differentiate these five species was not a problem. If it is assumed that 16S sequences with identity less than 95% should be assigned to different genera, these five sequences should actually be assigned to different genera.

TABLE 2

The abundance of species from unknown Lachnospiraceae genera in 10 human fecal samples

| Sample ID | 1 | 2 | 3 | 4 | 5 | 6 | 7 | 8 | 9 | 10 |
|---|---|---|---|---|---|---|---|---|---|---|
| f_Lachnospiraceae;g_NA | 2.8 | 8.3 | 4.9 | 5.8 | 4.4 | 15.1 | 11.6 | 9.8 | 11.3 | 6.4 |
| Sample ID | 1 | 2 | 3 | 4 | 5 | 6 | 7 | 8 | 9 | 10 |
| f_Lachnospiraceae;g_NA;s_sp32158 | | 0.1 | | | | | 0.1 | | | |
| f_Lachnospiraceae;g_NA;s_sp32167 | | 0.4 | 0.2 | 0.4 | 0.1 | 0.5 | 0.5 | 0.3 | 0.5 | 0.2 |
| f_Lachnospiraceae;g_NA;s_sp32172 | | | | | | 0.3 | | | | |
| f_Lachnospiraceae;g_NA;s_sp32262 | | | | 0.4 | | | | 0.1 | | |
| f_Lachnospiraceae;g_NA;s_sp32265 | | 0.6 | | 0.2 | | | 0.4 | 0.2 | 0.1 | 0.1 |
| f_Lachnospiraceae;g_NA;s_sp32277 | | 2.1 | 0.6 | 0.8 | 0.1 | 0.7 | 2.3 | 2.9 | 1.4 | 0.5 |
| f_Lachnospiraceae;g_NA;s_sp32490 | 0.1 | 0.1 | 0.1 | 0.1 | 0.1 | 0.1 | | 0.2 | | 0.2 |
| f_Lachnospiraceae;g_NA;s_sp32519 | 0.3 | 0.9 | 1.2 | 0.3 | 0.4 | 0.9 | 3.3 | 1.6 | 5.8 | 1.9 |
| f_Lachnospiraceae;g_NA;s_sp32615-sp32802 | | 0.5 | 0.1 | | | | | | | |
| f_Lachnospiraceae;g_NA;s_sp32640 | | 0.2 | 0.4 | 0.5 | 0.8 | | | 1.9 | | 0.6 |
| f_Lachnospiraceae;g_NA;s_sp32802 | | 0.6 | 0.1 | | | 0.1 | 0.1 | | | 0.2 |
| f_Lachnospiraceae;g_NA;s_sp32815 | | 0.1 | 0.3 | | | | | | | 0.3 |
| f_Lachnospiraceae;g_NA;s_sp32822 | 0.1 | | | 0.2 | 0.1 | | 0.7 | 0.6 | 0.7 | 0.1 |
| f_Lachnospiraceae;g_NA;s_sp32839 | | 1.0 | | | | | | | | |
| f_Lachnospiraceae;g_NA;s_sp32840 | | 0.1 | | | | | 0.3 | | 0.2 | 0.2 |
| f_Lachnospiraceae;g_NA;s_sp32859 | | | 0.2 | 0.1 | | 0.2 | | | | |
| f_Lachnospiraceae;g_NA;s_sp32907 | | 0.1 | | | | | 0.1 | | 0.3 | |
| f_Lachnospiraceae;g_NA;s_sp33271 | 0.1 | | | | | | 0.4 | | 0.1 | |
| f_Lachnospiraceae;g_NA;s_sp33275 | 0.6 | | | | | 10.5 | | | | |
| f_Lachnospiraceae;g_NA;s_sp33333 | 0.1 | 0.1 | 0.7 | 0.4 | 0.2 | 0.4 | 1.1 | 0.8 | 0.6 | 0.3 |
| f_Lachnospiraceae;g_NA;s_sp33357 | | | | | 1.3 | | | | | |
| f_Lachnospiraceae;g_NA;s_sp33371-sp33375 | | 0.1 | 0.2 | 0.3 | | 0.8 | 0.1 | 0.1 | 0.1 | 0.1 |
| f_Lachnospiraceae;g_NA;s_sp33374 | 0.8 | | | | | | | | | |
| f_Lachnospiraceae;g_NA;s_sp33375 | | | | 0.1 | | | | 0.1 | | |
| f_Lachnospiraceae;g_NA;s_sp33395 | 0.3 | 0.1 | 0.4 | 1.1 | 0.6 | 0.2 | 1.4 | 0.3 | 0.4 | 0.9 |
| f_Lachnospiraceae;g_NA;s_sp33439 | | 0.1 | | | | | 0.1 | | | 0.1 |
| f_Lachnospiraceae;g_NA;s_sp33454 | | 0.1 | | 0.1 | 0.1 | | | 0.1 | 0.2 | |
| f_Lachnospiraceae;g_NA;s_sp33470 | 0.1 | 0.1 | | 0.1 | | 0.1 | | 0.1 | 0.1 | 0.1 |
| f_Lachnospiraceae;g_NA;s_sp33517 | | | 0.3 | 0.2 | | | | 0.1 | 0.2 | |
| f_Lachnospiraceae;g_NA;s_sp33553 | | 0.1 | | 0.1 | | | 0.2 | 0.1 | 0.2 | 0.1 |
| f_Lachnospiraceae;g_NA;s_sp33656 | 0.1 | | | 0.1 | | | | | | |
| f_Lachnospiraceae;g_NA;s_sp33674 | | | | | | | | | | 0.3 |
| f_Lachnospiraceae;g_NA;s_sp33692 | | 0.1 | | 0.1 | | 0.1 | | 0.1 | | |
| f_Lachnospiraceae;g_NA;s_sp33751 | 0.1 | 0.1 | 0.1 | 0.1 | | | 0.1 | 0.1 | 0.2 | 0.2 |
| f_Lachnospiraceae;g_NA;s_sp33781 | | 0.4 | | | | | | | | |

TABLE 3

Sequence identity of taxonomy assignment and abundance of five species from unknown Lachnospiraceae genera that are commonly found in the 10 fecal samples

| Reference Species hits | Sp32519 | Sp32277 | Sp33395 | Sp33333 | Sp32167 |
|---|---|---|---|---|---|
| Representative Sequence derived from the data | Seq14 | Seq39 | Seq42 | Seq55 | Seq72 |
| Sequence Identity (%) | 99.8 | 99.8 | 99.8 | 99.8 | 100 |
| Average abundance (%) | 1.6 | 1.1 | 0.6 | 0.5 | 0.3 |

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

What is claimed is:

1. A method for the identification and/or quantification of one or more microbes comprising:
   (a) extracting DNA from a microbial sample;
   (b) performing 16S ribosomal RNA gene-targeted sequencing to obtain DNA sequences; and
   (c) analyzing the DNA sequences to identify the species of the one or more microbes,
   wherein the sequencing comprises using a pool of V1-V2 primers comprising SEQ ID NOs: 1-11 and/or a pool of V3-V4 primers comprising SEQ ID NOs: 12-19.

2. The method of claim 1, wherein the microbial sample is a human sample.

3. The method of claim 1, wherein the microbial sample is an environmental sample.

4. The method of claim 3, wherein the environmental sample comprises water, biofilms, soil, air, or host-derived samples.

5. The method of claim 4, wherein the host-derived sample comprises body fluids, saliva, urine, fecal, root, leaf or bark samples.

6. The method of claim 4, wherein the host-derived sample is a fecal sample.

7. The method of claim 1, wherein step (b) comprises amplifying the 16S rRNA sequences.

8. The method of claim 7, wherein qPCR is used to monitor the efficiency of the amplification.

9. The method of claim 1, wherein analyzing DNA sequences is further defined as performing bioinformatics analysis to identify the species of the one or more microbes.

10. The method of claim 9, wherein a subset of amplicon sequences are used for analysis.

11. The method of claim 10, wherein every about $2^{nd}$, $3^{rd}$, $4^{th}$, $5^{th}$, $10^{th}$, $15^{th}$, $20^{th}$, $25^{th}$, $30^{th}$ $40^{th}$ or $50^{th}$ amplicon is analyzed.

12. The method of claim 9, wherein the bioinformatics analysis comprises using FIGARO to trim amplicon sequences.

13. The method of claim 9, wherein the bioinformatics analysis comprises using DADA2 to infer amplicon sequences.

14. The method of claim 9, wherein the bioinformatics analysis comprises using FIGARO to trim amplicon sequences and then DADA2 to infer amplicon sequences.

15. The method of claim 13, wherein the bioinformatics analysis further comprises assigning taxonomy to amplicon sequences.

16. The method of claim 15, wherein assigning taxonomy does not comprise clustering amplicon sequences into operation units (OTUs).

17. The method of claim 15, wherein assigning taxonomy comprises using hits with higher sequence identity.

18. The method of claim 1, wherein the method is performed in less than 3 days.

19. The method of claim 1, wherein the method is performed in 2 days.

20. The method of claim 1, wherein the method does not comprise microbial culture or array analysis.

21. The method of claim 1, wherein the one or more microbes are of the phylum *Euryarchaeota, Actinobacteria, Bacteroidetes, Firmicutes, Fusobacteria, Lentisphaerae, Proteobacteria, Synergistetes, and/or Verrucomicrobia*.

22. The method of claim 1, wherein the one or more microbes are of the genus *Blautia, Butyrivibrio, Coprococcus, Dorea, Eubacterium, Fusicatenibacter, Lachnoclostridium, Lachnospira, Pseudobutyrivibrio, and/or Roseburia*.

23. The method of claim 1, wherein the one or more microbes are of the species *Methanobrevibacter smithii, Bifidobacterium adolescentis, Bifidobacterium angulatum, Bifidobacterium ruminantium, Collinsella aerofaciens, Bacteroides fragilis, Prevotella copri, Sphingobacteriaceae sp., Catenibacterium mitsuokai, Clostridium difficile, Dialister invisus, Eubacterium rectale, Lactobacillus fermentum, Fusobacterium nucleatum, Victivallis vadensis, Bilophila wadsworthia, Escherichia coli, Sutterella wadsworthensis, Pyramidobacter piscolens, and/or Akkermansia muciniphila*.

24. The method of claim 1, wherein the sequencing comprises using the V3-V4 primer pool.

\* \* \* \* \*

SEQUENCE LISTING

<160> NUMBER OF SEQ ID NOS: 19

<210> SEQ ID NO 1

-continued

```
<211> LENGTH: 20
<212> TYPE: DNA
<213> ORGANISM: Artificial sequence
<220> FEATURE:
<223> OTHER INFORMATION: Synthetic primer

<400> SEQUENCE: 1
agrgtttgat ymtggctcag                                              20

<210> SEQ ID NO 2
<211> LENGTH: 20
<212> TYPE: DNA
<213> ORGANISM: Artificial sequence
<220> FEATURE:
<223> OTHER INFORMATION: Synthetic primer

<400> SEQUENCE: 2
agggttcgat tctggctcag                                              20

<210> SEQ ID NO 3
<211> LENGTH: 20
<212> TYPE: DNA
<213> ORGANISM: Artificial sequence
<220> FEATURE:
<223> OTHER INFORMATION: Synthetic primer

<400> SEQUENCE: 3
agaatttgat cttggttcag                                              20

<210> SEQ ID NO 4
<211> LENGTH: 20
<212> TYPE: DNA
<213> ORGANISM: Artificial sequence
<220> FEATURE:
<223> OTHER INFORMATION: Synthetic primer

<400> SEQUENCE: 4
agagttcgat cctggctcag                                              20

<210> SEQ ID NO 5
<211> LENGTH: 20
<212> TYPE: DNA
<213> ORGANISM: Artificial Sequence
<220> FEATURE:
<223> OTHER INFORMATION: Synthetic primer

<400> SEQUENCE: 5
agagtttgat cctggcttag                                              20

<210> SEQ ID NO 6
<211> LENGTH: 20
<212> TYPE: DNA
<213> ORGANISM: Artificial Sequence
<220> FEATURE:
<223> OTHER INFORMATION: Synthetic primer

<400> SEQUENCE: 6
agagtttgat cctagctcag                                              20

<210> SEQ ID NO 7
<211> LENGTH: 19
```

```
<212> TYPE: DNA
<213> ORGANISM: Artificial Sequence
<220> FEATURE:
<223> OTHER INFORMATION: Synthetic primer

<400> SEQUENCE: 7
actgctattg ggdttcgat                                                  19

<210> SEQ ID NO 8
<211> LENGTH: 19
<212> TYPE: DNA
<213> ORGANISM: Artificial Sequence
<220> FEATURE:
<223> OTHER INFORMATION: Synthetic primer

<400> SEQUENCE: 8
actgctattg gggtccgat                                                  19

<210> SEQ ID NO 9
<211> LENGTH: 19
<212> TYPE: DNA
<213> ORGANISM: Artificial Sequence
<220> FEATURE:
<223> OTHER INFORMATION: Synthetic primer

<400> SEQUENCE: 9
tbaccgcggc tgctggcac                                                  19

<210> SEQ ID NO 10
<211> LENGTH: 19
<212> TYPE: DNA
<213> ORGANISM: Artificial Sequence
<220> FEATURE:
<223> OTHER INFORMATION: Synthetic primer

<400> SEQUENCE: 10
ttaccgcggc ggctgrcac                                                  19

<210> SEQ ID NO 11
<211> LENGTH: 19
<212> TYPE: DNA
<213> ORGANISM: Artificial Sequence
<220> FEATURE:
<223> OTHER INFORMATION: Synthetic primer

<400> SEQUENCE: 11
ttaccgcagc tgctggcac                                                  19

<210> SEQ ID NO 12
<211> LENGTH: 17
<212> TYPE: DNA
<213> ORGANISM: Artificial Sequence
<220> FEATURE:
<223> OTHER INFORMATION: Synthetic primer

<400> SEQUENCE: 12
cctacgggdg gcwgcag                                                    17

<210> SEQ ID NO 13
<211> LENGTH: 17
<212> TYPE: DNA
```

```
<213> ORGANISM: Artificial Sequence
<220> FEATURE:
<223> OTHER INFORMATION: Synthetic primer

<400> SEQUENCE: 13 cctaygggc gcwgcag                                                    17

<210> SEQ ID NO 14
<211> LENGTH: 17
<212> TYPE: DNA
<213> ORGANISM: Artificial Sequence
<220> FEATURE:
<223> OTHER INFORMATION: Synthetic primer

<400> SEQUENCE: 14
cctacggggt gcagcag                                                   17

<210> SEQ ID NO 15
<211> LENGTH: 17
<212> TYPE: DNA
<213> ORGANISM: Artificial Sequence
<220> FEATURE:
<223> OTHER INFORMATION: Synthetic primer

<400> SEQUENCE: 15
cctacgggag gctgcag                                                   17

<210> SEQ ID NO 16
<211> LENGTH: 21
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (7)..(7)
<223> OTHER INFORMATION: n is a, c, g, or t

<400> SEQUENCE: 16
gactacnvgg gtmtctaatc c                                              21

<210> SEQ ID NO 17
<211> LENGTH: 21
<212> TYPE: DNA
<213> ORGANISM: Artificial Sequence
<220> FEATURE:
<223> OTHER INFORMATION: Synthetic primer

<400> SEQUENCE: 17
gactacdcag gtctctaatc t                                              21

<210> SEQ ID NO 18
<211> LENGTH: 21
<212> TYPE: DNA
<213> ORGANISM: Artificial Sequence
<220> FEATURE:
<223> OTHER INFORMATION: Synthetic primer

<400> SEQUENCE: 18
gamtaccggg gtttctaatc c                                              21
```

```
<210> SEQ ID NO 19
<211> LENGTH: 21
<212> TYPE: DNA
<213> ORGANISM: Artificial Sequence
<220> FEATURE:
<223> OTHER INFORMATION: Synthetic primer

<400> SEQUENCE: 19
gactaccagg gtatctaagc c                                                    21
```